US009192933B2

(12) United States Patent
Whitesides et al.

(10) Patent No.: US 9,192,933 B2
(45) Date of Patent: Nov. 24, 2015

(54) MICROFLUIDIC, ELECTROCHEMICAL DEVICES

(75) Inventors: George M. Whitesides, Newton, MA (US); Zhihong Nie, Cambridge, MA (US); Christian Nijhuis, Somerville, MA (US); Xin Chen, Cambridge, MA (US); Andres W. Martinez, Cambridge, MA (US); Max Narovlyansky, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 808 days.

(21) Appl. No.: 13/254,967

(22) PCT Filed: Mar. 8, 2010

(86) PCT No.: PCT/US2010/026499
§ 371 (c)(1),
(2), (4) Date: Apr. 4, 2012

(87) PCT Pub. No.: WO2010/102279
PCT Pub. Date: Sep. 10, 2010

(65) Prior Publication Data
US 2012/0181184 A1 Jul. 19, 2012

Related U.S. Application Data

(60) Provisional application No. 61/158,251, filed on Mar. 6, 2009.

(51) Int. Cl.
*G01N 27/26* (2006.01)
*B01L 3/00* (2006.01)
*G01N 27/327* (2006.01)

(52) U.S. Cl.
CPC .............. *B01L 3/5027* (2013.01); *B01L 3/502* (2013.01); *G01N 27/3272* (2013.01); *B01L 2300/0645* (2013.01); *B01L 2300/0887* (2013.01)

(58) Field of Classification Search
CPC ............ B01L 3/5027; B01L 3/502715; B01L 2300/0887; B01L 2300/0645; G01N 15/1484; G01N 27/3272
See application file for complete search history.

(56) References Cited

U.S. PATENT DOCUMENTS
4,618,475 A 10/1986 Wang
4,668,564 A 5/1987 Orchard
(Continued)

FOREIGN PATENT DOCUMENTS
EP 2143491 1/2010
JP 08233799 A 9/1996
(Continued)

OTHER PUBLICATIONS
Aikio, et al., "Bioactive Paper and Fibre Products: Patent and Literary Survey," VTT Working Papers 51, VTT-Work-51, 2006, 84 pages.
Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.
(Continued)

*Primary Examiner* — Gurpreet Kaur
(74) *Attorney, Agent, or Firm* — Wilmer Cutler Pickering Hale and Dorr LLP

(57) ABSTRACT

Microfluidic, electrochemical devices are described. The microfluidic, electrochemical device comprises one or more electrode(s) on a substrate and a patterned porous, hydrophilic layer having a fluid-impermeable barrier which substantially permeates the thickness of the porous, hydrophilic layer and defines boundaries of one or more hydrophilic channels within the patterned porous, hydrophilic layer, wherein the hydrophilic channel(s) comprises a hydrophilic region which is in fluidic communication with the electrode(s). In some embodiments, the electrodes comprise a working electrode, a counter electrode, and a reference electrode. In some embodiments, the microfluidic, electrochemical device further comprises a fluid sink. The method of assembling the microfluidic, electrochemical device is described. The method of using the device for electrochemical analysis of one or more analytes is also described.

26 Claims, 10 Drawing Sheets

(56) References Cited

U.S. PATENT DOCUMENTS

| | | | |
|---|---|---|---|
| 4,668,619 A | 5/1987 | Greenquist et al. | |
| 4,743,530 A | 5/1988 | Farid et al. | |
| 4,757,004 A | 7/1988 | Houts et al. | |
| 4,861,711 A | 8/1989 | Friesen et al. | |
| 5,120,544 A | 6/1992 | Henley | |
| 5,209,904 A | 5/1993 | Forney et al. | |
| 5,266,179 A | 11/1993 | Nankai et al. | |
| 5,279,944 A | 1/1994 | Fabrizi et al. | |
| 5,409,664 A | 4/1995 | Allen | |
| 5,648,252 A | 7/1997 | Dumitriu et al. | |
| 5,707,818 A | 1/1998 | Chudzik et al. | |
| 5,834,226 A | 11/1998 | Maupin | |
| 5,858,392 A | 1/1999 | Dumitriu et al. | |
| 5,869,172 A | 2/1999 | Caldwell | |
| 5,897,522 A | 4/1999 | Nitzan | |
| 5,906,934 A | 5/1999 | Grande et al. | |
| 5,925,259 A | 7/1999 | Biebuyck et al. | |
| 5,941,862 A | 8/1999 | Haynes et al. | |
| 5,997,817 A * | 12/1999 | Crismore et al. | 204/403.1 |
| 6,004,442 A | 12/1999 | Choulga et al. | |
| 6,025,203 A | 2/2000 | Vetter et al. | |
| 6,060,534 A | 5/2000 | Ronan et al. | |
| 6,180,239 B1 | 1/2001 | Whitesides et al. | |
| 6,202,471 B1 | 3/2001 | Yadav et al. | |
| 6,210,907 B1 | 4/2001 | Cha | |
| 6,284,072 B1 | 9/2001 | Ryan et al. | |
| 6,319,310 B1 | 11/2001 | Wong et al. | |
| 6,391,523 B1 | 5/2002 | Hurditch et al. | |
| 6,416,642 B1 | 7/2002 | Alajoki et al. | |
| 6,440,645 B1 | 8/2002 | Yon-Hin et al. | |
| 6,440,725 B1 | 8/2002 | Pourahmadi et al. | |
| 6,478,938 B1 | 11/2002 | Paek et al. | |
| 6,566,575 B1 | 5/2003 | Stickels et al. | |
| 6,642,408 B2 | 11/2003 | Batlaw et al. | |
| 6,761,962 B2 | 7/2004 | Bentsen et al. | |
| 6,783,735 B2 | 8/2004 | Vanmaele et al. | |
| 6,790,341 B1 * | 9/2004 | Saban et al. | 205/775 |
| 6,816,125 B2 | 11/2004 | Kuhns et al. | |
| 6,844,200 B2 | 1/2005 | Brock | |
| 6,877,892 B2 | 4/2005 | Karp | |
| 6,880,576 B2 | 4/2005 | Karp et al. | |
| 6,887,701 B2 | 5/2005 | Anderson et al. | |
| 6,919,046 B2 | 7/2005 | O'Connor et al. | |
| 6,931,523 B1 | 8/2005 | Tomoson et al. | |
| 6,935,772 B2 | 8/2005 | Karp et al. | |
| 6,951,682 B1 | 10/2005 | Zebala | |
| 6,951,757 B2 | 10/2005 | Sabatini | |
| 6,989,128 B2 | 1/2006 | Alajoki et al. | |
| 7,008,799 B1 | 3/2006 | Zimmer et al. | |
| 7,063,776 B2 * | 6/2006 | Huang | 204/403.14 |
| 7,186,352 B2 | 3/2007 | Morse et al. | |
| 7,192,693 B2 | 3/2007 | Bryant | |
| 7,291,857 B2 | 11/2007 | Tanaka et al. | |
| 7,303,923 B2 | 12/2007 | Hardman et al. | |
| 8,206,992 B2 | 6/2012 | Reches et al. | |
| 2002/0187074 A1 | 12/2002 | O'Connor et al. | |
| 2002/0187560 A1 | 12/2002 | Pezzuto et al. | |
| 2003/0032203 A1 | 2/2003 | Sabatini et al. | |
| 2003/0148401 A1 | 8/2003 | Agrawal et al. | |
| 2004/0067166 A1 | 4/2004 | Karinka et al. | |
| 2004/0103808 A1 | 6/2004 | Lochun et al. | |
| 2004/0119070 A1 | 6/2004 | Roach et al. | |
| 2005/0136501 A1 | 6/2005 | Kuriger | |
| 2005/0145496 A1 | 7/2005 | Goodsaid et al. | |
| 2005/0169962 A1 | 8/2005 | Bhatia et al. | |
| 2005/0196702 A1 | 9/2005 | Bryant et al. | |
| 2005/0266582 A1 | 12/2005 | Modlin et al. | |
| 2006/0014003 A1 | 1/2006 | Libera et al. | |
| 2006/0038182 A1 | 2/2006 | Rogers et al. | |
| 2006/0088857 A1 | 4/2006 | Attiya et al. | |
| 2006/0130054 A1 | 6/2006 | Bocking et al. | |
| 2006/0226575 A1 | 10/2006 | Maghribi et al. | |
| 2007/0179117 A1 | 8/2007 | Reiner et al. | |
| 2007/0196819 A1 | 8/2007 | Asberg et al. | |
| 2007/0224701 A1 | 9/2007 | Rosenstein | |
| 2007/0278097 A1 | 12/2007 | Bhullar et al. | |
| 2007/0298433 A1 | 12/2007 | Sia et al. | |
| 2009/0298191 A1 | 12/2009 | Whitesides et al. | |
| 2011/0111517 A1 | 5/2011 | Siegel et al. | |
| 2011/0123398 A1 | 5/2011 | Carrilho et al. | |
| 2011/0189786 A1 | 8/2011 | Reches et al. | |
| 2012/0198684 A1 | 8/2012 | Carrilho et al. | |

FOREIGN PATENT DOCUMENTS

| | | |
|---|---|---|
| WO | WO-97/48257 | 12/1997 |
| WO | WO-99/46644 | 9/1999 |
| WO | WO-0033078 | 6/2000 |
| WO | WO-01/02093 A2 | 1/2001 |
| WO | WO-01/25138 | 4/2001 |
| WO | WO-03/015890 A1 | 2/2003 |
| WO | WO-2004/006291 A2 | 1/2004 |
| WO | WO-2004/080138 | 9/2004 |
| WO | WO-2005/090975 A1 | 9/2005 |
| WO | WO-2005/090983 A2 | 9/2005 |
| WO | WO-2005/107938 | 11/2005 |
| WO | WO-2005/109005 A1 | 11/2005 |
| WO | WO-2006/018044 | 2/2006 |
| WO | WO-2006/076703 | 7/2006 |
| WO | WO-2007/029250 | 3/2007 |
| WO | WO-2007/081848 | 7/2007 |
| WO | WO-2007/116056 | 10/2007 |
| WO | WO-2008/049083 | 4/2008 |
| WO | WO-2009/120963 | 10/2009 |
| WO | WO-2009/121037 A2 | 10/2009 |
| WO | WO-2009/121038 | 10/2009 |
| WO | WO-2009/121041 A2 | 10/2009 |
| WO | WO-2009/121043 A2 | 10/2009 |
| WO | WO-2010/022324 | 2/2010 |
| WO | WO-2010/102279 A1 | 9/2010 |
| WO | WO-2010/102294 A1 | 9/2010 |
| WO | WO-2011/097412 | 8/2011 |

OTHER PUBLICATIONS

Berggren, et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, 5 Pages.

Brooks, et al., "A Simple Artificial Urine for the Growth of Urinary Pathogens," Lett. Appl. Microbiol., 1997, 24, pp. 203-206.

Bruzewicz, et al., "Low-Cost Printing of Poly(dimethylsiloxane) Barriers to Define Microchannels in Paper," Anal. Chem., 2008, 80, pp. 3387-3392.

Bruzewicz, et al., "Paper: Fabrication of a Modular Tissue Construct in a Microfluidic Chip," Lab Chip, 2008, 8, pp. 663-671.

Campana, et al., "Double and Triple Staining Methods for Studying the Proliferative Activity of Human B and T Lymphoid Cells," Journal of Immunological Methods, 107, 1988, pp. 79-88.

Carrilho, et al., "Paper Microzone Plates," Analytical Chemistry, vol. 81, No. 15, Aug. 2009, pp. 5990-5998.

Carrilho, et al., "Understanding Wax Printing: A Simple Micropatterning Process for Paper-Based Microfluidics," Analytical Chemistry, vol. 81, No. 16, Aug. 2009, pp. 7091-7095.

Chadee, et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.

Cheng, et al., "Clinical Analytics: Paper-Based ELISA," Agnew. Chem., 2010, 122, pp. 1-5.

Chin, et al., "Lab-on-a-chip Devices for Global Health: Past Studies and Future Opportunities," Lab Chip, 2007, 7, pp. 41-57, A Journal of The Royal Society of Chemistry.

Costerton, et al., "Bacterial Biofilms: a Common Cause of Persistent Infections," Science Mag., 1999, pp. 1318-1322.

Daar, et al., "Top Ten Biotechnologies for Improving Health in Developing Countries," Nature Genetics, vol. 32, Oct. 2002, pp. 229-232.

Derda, et al., "Paper-supported 3D Cell Culture for Tissue-Based Bioassays," PNAS, vol. 106, No. 44, Nov. 2009, pp. 18457-18462.

(56) References Cited

OTHER PUBLICATIONS

Donlan, "Biofilm Formation: A Clinically Relevant Microbiological Process," Healthcare Epidemiology, CID 2001:33, Oct. 2001, pp. 1387-1392.
Donlan, et al., "Biofilm Formation on Cast Iron Substrata in Water Distribution Systems," Wat. Res. vol. 28, No. 6, pp. 1497-1503, 1994.
Donlan, et al., "Reviews: Biofilms: Survival Mechanisms of Clinically Relevant Microorganisms," Clinical Microbiology Reviews, vol. 15, No. 2, Apr. 2002, pp. 167-193.
Dungchai, et al., "Electrochemical Detection for Paper-Based Microfluidics," Anal. Chem., 2009, 81, pp. 5821-5826.
Ebeling, "The Permanent Life of Connective Tissue Outside of the Organism," J. Exp. Med., 17, 1913, 15 pages.
Harrison, et al., "Methodology Article: High-Throughput Metal Susceptibility Testing of Microbial Biofilms," BMC Microbiology, 2005, 5:53, 11 pages.
International Search Report and Written Opinion of the International Searching Authority, the European Patent Office, for International Application No. PCT/US2007/081848, dated Jan. 28, 2009, 12 pages.
International Search Report and Written Opinion of the International Searching Authority, the European Patent Office, for PCT/US2010/026499, dated Jun. 16, 2010, 2 pages.
International Search Report and Written Opinion of the International Searching Authority, the Korean Intellectual Property Office, for International Application No. PCT/US2009/038566, dated Dec. 16, 2009, 10 pages.
International Search Report and Written Opinion of the International Searching Authority, the Korean Intellectual Property Office, for International Application No. PCT/US2009/038694 dated Nov. 12, 2009, 10 pages.
International Search Report and Written Opinion of the International Searching Authority, the Korean Intellectual Property Office, for PCT/US2009/038693, dated Oct. 28, 2009, 8 pages.
International Search Report and Written Opinion of the International Searching Authority, the Korean Intellectual Property Office, for PCT/US2009/038699, dated Oct. 28, 2009, 9 pages.
International Search Report and Written Opinion of the International Searching Authority, the Korean Intellectual Property Office, for PCT/US2009/038702, dated Nov. 11, 2009, 7 pages.
International Search Report of the International Searching Authority, the European Patent Office, for PCT/US2010/026547, dated Jul. 19, 2010, 3 pages.
International Search Report of the International Searching Authority, the Korean Intellectual Property Office, for PCT/US2009/054601, dated Mar. 22, 2010, 2 pages.
Klajn, et al., "Multicolour Micropatterning of Thin Films and Dry Gels," Nature Materials, vol. 3, Oct. 2004, pp. 729-735.
Lahav, et al., "DOI: 10.1002/adma.200601843—Patterning of Poly(acrylic acid) by Ionic Exchange Reactions in Microfluidic Channels," Advanced Materials, 2006, 18, pp. 3174-3178.
Leary, et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.
Li, et al., "Thread as a Versatile Material for Low-Cost Microfluidic Diagnostics," Applied Materials & Interfaces, vol. 2, No. 1, Jan. 2010, 6 pages.
Liu, et al., "Three-Dimensional Photopatterning of Hydrogels Containing Living Cells," Biomed. Microdevices, 2002, 4, pp. 257-266.
Lu, et al., "Short Communication: Rapid Prototyping of Paper-Based Microfluidics with Wax for Low-Cost, Portable Bioassay," Electrophoresis, 2009, 30, pp. 1497-1500.
Mabey, et al., "Diagnostics for the Developing World," Nature Reviews / Microbiology, vol. 2, Mar. 2004, pp. 231-240.
Martinez, et al., "Diagnostics for the Developing World: Microfluidic Paper-Based Analytical Devices," Analytical Chemistry, vol. 82, No. 1, Jan. 2010, pp. 3-10.
Martinez, et al., "FLASH: A Rapid Method for Prototyping Paper-Based Microfluidic Devices," Lab Chip, 2008, 8, pp. 2146-2150, A Journal of The Royal Society of Chemistry.
Martinez, et al., "Paper: Programmable Diagnostic Devices Made from Paper and Tape," Lab Chip, Jul. 2010, 6 pages.
Martinez, et al., "Patterned Paper as a Platform for Inexpensive, Low-Volume, Portable Bioassays," Agnew. Chem. Int. Ed., 2007, 46, pp. 1318-1320.
Martinez, et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.
Martinez, et al., "Three-Dimensional Microfluidic Devices Fabricated in Layered Paper and Tape," PNAS, vol. 105, No. 50, Dec. 2008, pp. 19606-19611.
Matsumoto, et al., "Three-Dimensional Cell and Tissue Patterning in a Strained Fibrin Gel System," PLoS One, Nov. 2007, Issue No. 11, 6 pages.
Nelson, et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.
Nie et al., "Paper: Integration of Paper-based Microfluidic Devices with Commercial Electrochemical Readers," Lab Chip, Oct. 2010, 7 pages.
Peele, et al., "Semi-Automated vs. Visual Reading of Urinalysis Dipsticks," Clin. Chem., 1977, 23, pp. 2242-2246.
Pugia, et al., "High-Sensitivity Dye Binding Assay for Albumin in Urine," J. Clin. Lab. Anal. 1999, 13, pp. 180-187.
Reches, et al., "Thread as a Matrix for Biomedical Assays," Applied Materials & Interfaces, 2010, pp. A-G, (7 Pages).
Shaw, et al., "Negative Photoresists for Optical Lithography," IBM Journal of Research and Development, vol. 41, No. ½, Jan./Mar. 1997, pp. 81-94, 15 pages.
Shimizu, et al., "Biofilm Formation on Hydrophilic Intraocular Lens Material," Current Eye Research, 31, 2006, pp. 989-997.
Sia, et al., "Microfluidic Devices Fabricated in Poly(dimethylsiloxane) for Biological Studies," Electrophoresis, 2003, 24, pp. 3563-3576.
Siegel, et al., "Foldable Printed Circuit Boards on Paper Substrates," Advanced Functional Materials, 2010, 20, pp. 28-35.
Smith, S.K., "Angiogenesis, Vascular Endothelial Growth Factor and the Endometrium," Hum. Reprod. Update 1998, 4, pp. 509-519.
Supplementary European Search Report and Written Opinion for European Application No. 09724164 dated Mar. 16, 2011, 7 pages.
Tang, et al., "Molding of Three-Dimensional Microstructures of Geis," J. Am. Chem. Soc., 2003, 125, pp. 12988-12989.
Urbich, et al., "Endothelial Progenitor Cells: Characterization and Role in Vascular Biology," Circulation Research, DOI: 10.1161/01.RES.0000137877.89448.78, Aug. 2004, pp. 343-353.
von Lode, P., "Point-of-care Immunotesting: Approaching the Analytical Performance of Central Laboratory Methods," Clinical Biochemistry, 38, 2005, pp. 591-606.
Washburn, E. W., "The Dynamics of Capillary Flow," The Physical Review, vol. XVII, No. 3, Second Series, Mar. 1921, pp. 273-283.
Winkleman, et al., "Patterning micron-sized features in a cross-linked poly (acrylic acid) film by a wet etching process," The Royal Society of Chemistry, 2007, pp. 108-116.
Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf.
Zhi, et al., "Multianalyte Immunoassay with Self-Assembled Addressable Microparticle Array on a Chip," Analytical Biochemistry, vol. 318, No. 2, Jul. 2003, pp. 236-243.
Zhu, et al., "Research Article: Proposal to Create Subspecies of Rickettsia Conorii Based on Multi-Locus Sequence Typing and an Emended Description of Rickettsia Conorii," BMC Microbiology, 2005, 5:11, 11 pages.
Muller et al., "Automatic Paper Chromatography," Analytical Chemistry, vol. 21, No. 9, Sep. 1949, pp. 1123-1125.
Carvalhal, R.F. et al., "Electrochemical Detection in a Paper-Based Separation Device," Analytical Chemistry, vol. 82, No. 3, pp. 1162-1165 (Jan. 7, 2010).

\* cited by examiner

MICROFLUIDIC, ELECTROCHEMICAL DEVICES

RELATED APPLICATIONS

This application claims the benefit of U.S. Provisional Patent Application No. 61/158,251, filed Mar. 6, 2009, which is hereby incorporated by reference in its entirety. This application is related to copending PCT Application, titled "Methods Of Micropatterning Paper-Based Microfluidics," filed on Mar. 8, 2010, Publication No. WO 2010/102294, which is incorporated in its entirety by reference.

BACKGROUND

The disclosed subject matter relates generally to microfluidic devices.

In recent years, microfluidic systems have attracted increasing interests due to their diverse and widespread potential applications. For example, using very small volumes of samples, microfluidic systems could carry out complicated biochemical reactions to acquire important chemical and biological information. Among other advantages, microfluidic systems reduce the required amount of samples and reagents, shorten the response time of reactions, and decrease the amount of biohazard waste for disposal.

First developed in the early 1990s, microfluidic devices were initially fabricated in silicon and glass using photolithography and etching techniques adapted from the microelectronics industry. Current microfluidic devices are constructed from plastic, silicone, or other polymeric materials, e.g. polydimethylsiloxane (PDMS). Such devices are generally expensive, inflexible, and difficult to construct.

Electrochemical analysis involves methods of measuring the potential and/or current of a fluidic sample containing analytes, which is widely used in the medicinal field or in environmental studies. Electrochemical analysis usually utilizes sophisticated instruments and is conducted by specially-trained technicians. However, for use in developing countries, in the field, or in-home heath-care settings, there remains a need for analytical devices that are inexpensive, portable, and easy to construct and use.

SUMMARY OF THE INVENTION

Microfluidic, electrochemical devices are described.

In one aspect, a microfluidic, electrochemical device is described, including:

a first electrode assembly including a first substrate layer supporting one or more electrodes; and a first porous, hydrophilic layer overlaying the electrode assembly, wherein the hydrophilic layer includes a fluid-impermeable boundary that substantially permeates the thickness of the hydrophilic layer and defines a one or more hydrophilic channels within the hydrophilic layer, wherein the one or more hydrophilic channels include a first hydrophilic region which is in fluidic communication with the one or more electrodes.

In some embodiments, the electrode assembly further includes a barrier material surrounding at least a portion of the electrode.

In any of the preceding embodiments, the microfluidic, electrochemical further includes:

a fluid-impermeable layer overlaying and contacting at least a portion of the first hydrophilic layer; and a second porous, hydrophilic layer overlaying and contacting at least a portion of the fluid-impermeable layer, wherein the second hydrophilic layer including a fluid-impermeable boundary that substantially permeates the thickness of the second hydrophilic layer and defines one or more hydrophilic channels within the second hydrophilic layer, wherein the fluid-impermeable layer includes one or more openings in alignment with and in fluidic communication with at least a portion of a hydrophilic channel within each hydrophilic layer.

In any of the preceding embodiments, a porous, hydrophilic medium is disposed in the opening of the first fluid-impermeable layer and is in fluidic communication with at least a portion of a hydrophilic channel within the hydrophilic layers.

In any of the preceding embodiments, the electrode assembly includes a working electrode and a counter electrode.

In any of the preceding embodiments, the first electrode assembly includes a working electrode and the microfluidic, electrochemical device further includes a second electrode assembly including a counter electrode including a second substrate layer supporting the counter electrode, wherein the counter electrode is substantially surrounded by a barrier material.

In any of the preceding embodiments, the first porous, hydrophilic layer including the first hydrophilic region is disposed between the first and the second electrode assemblies, and wherein the first hydrophilic region is in fluidic communication with both the working and counter electrodes.

In any of the preceding embodiments, the microfluidic, electrochemical device further includes a fluid sink, wherein the fluid sink is in fluidic communication with one end of the hydrophilic channel including the first hydrophilic region.

In any of the preceding embodiments, the fluid sink includes a blotting cellulose paper.

In any of the preceding embodiments, the porous, hydrophilic medium includes paper.

In any of the preceding embodiments, the first or second porous, hydrophilic layer includes paper.

In any of the preceding embodiments, the first or second substrate layer includes a paper or a plastic film.

In any of the preceding embodiments, the barrier material includes polymerized photoresist disposed on the paper or plastic film and substantially surrounding the electrode.

In any of the preceding embodiments, the barrier material includes a fluid-impermeable sheet having apertures of a dimension for receiving the electrode, said fluid-impermeable sheet disposed over the first or second substrate layer and substantially surrounding the electrode.

In any of the preceding embodiments, the first or second substrate layer are integral with and form a unitary body with the barrier material.

In any of the preceding embodiments, the fluid-impermeable sheet includes double-sided adhesive tape.

In any of the preceding embodiments, the fluid-impermeable layer includes adhesive tape.

In any of the preceding embodiments, the first or second electrode assembly further includes a reference electrode.

In another aspect, a method of preparing a microfluidic, electrochemical device is described, including:

disposing a layer of hydrophobic barrier including a stencil including one or more openings to a supporting layer;

depositing electro-conductive material in the opening(s) to form one or more electrode(s); and attaching a porous, hydrophilic layer including a fluid-impermeable barrier that substantially permeates the thickness of the patterned porous, hydrophilic layer and} defines a boundary of one or more hydrophilic channel(s) in the porous, hydrophilic layer; wherein the hydrophilic channel includes a first hydrophilic region; and the first hydrophilic region is in fluidic communication with the electrode(s).

In any of the preceding embodiments, the method further includes:

attaching one or more porous, hydrophilic layer including a fluid-impermeable barrier that substantially permeates the thickness of the patterned porous, hydrophilic layer and defines a boundary of one or more hydrophilic channel(s) in the patterned porous, hydrophilic layer; and disposing a second fluid-impermeable layer between adjacent patterned porous, hydrophilic layers; wherein the second fluid-impermeable layer includes one or more openings; and each opening is in alignment with and in fluidic communication with one or more portion(s) of one of the hydrophilic channel(s).

In yet another aspect, a method of determining the presence of one or more analytes in a fluidic sample using a microfluidic, electrochemical device of any one of the preceding embodiments, including:

depositing a fluidic sample in one of the one or more hydrophilic channels of the porous, hydrophilic layer to provide fluidic contact of the sample with the electrode(s); and measuring an electrochemical signal using the electrode(s).

In any of the preceding embodiments, the electrochemical signal is correlated with a concentration of the analyte(s).

In any of the preceding embodiments, the electrochemical signal is correlated with presence of the analyte(s).

In any of the preceding embodiments, the fluidic sample is deposited in a region of the hydrophilic channel positioned substantially over the one or more electrode(s).

In any of the preceding embodiments, the microfluidic, electrochemical device further includes a fluid sink in fluidic communication with a distal end of the hydrophilic channel including the first hydrophilic region; and the method further including:

depositing the fluidic sample at a proximal end of the hydrophilic channel comprising the first hydrophilic region; wherein the fluidic sample is transported through capillary action over the electrode and into the fluid sink; and wherein a constant fluidic flow of the fluidic sample is maintained across the electrode(s).

In any of the preceding embodiments, measuring an electrochemical signal includes impedance measurement, current measurement or voltage.

In any of the preceding embodiments, the electrochemical measurement is selected from the group consisting of amperometry, biamperometry, stripping voltammetry, differential pulse voltammetry, cyclic voltammetry, coulometry, chronoamperometry, and potentiometry.

In any of the preceding embodiments, the electrochemical measurement is chronoamperometry and the analyte includes glucose, cholesterol, uric acid, lactate, blood gases, DNA, haemoglobin, nitric oxide, and blood ketones.

In any of the preceding embodiments, measuring an electrochemical signal includes anodic stripping voltammetry.

In any of the preceding embodiments, the analyte includes a heavy metal ion or a mixture of heavy metal ions.

As used herein, "3-D" and "three-dimensional" are used interchangeably.

As used herein, "µPED" refers to a microfluidic, paper-based electrochemical device. As used herein, "F-F µPED" refers to a face-to-face microfluidic, paper-based electrochemical device. As used herein, "S-S µPED" refers to a side-by-side microfluidic, paper-based electrochemical device.

BRIEF DESCRIPTION OF THE DRAWINGS

Non-limiting embodiments of the present invention will be described by way of examples with reference to the accompanying figures, in which:

FIG. 1(a) illustrates a perspective view of the device; FIG. 1(b) illustrates a top view of the device;

FIG. 2(a) illustrates a top view of the device; FIG. 1(b) illustrates a side view of the device;

FIG. 3(a) illustrates a schematic view of the device; FIG. 3(b) illustrates a top view of the device;

DETAILED DESCRIPTION

In one aspect, a microfluidic, electrochemical device is described. The microfluidic, electrochemical device comprises a first electrode assembly and a first porous, hydrophilic layer. The first electrode assembly comprises a first substrate layer which supports one or more electrode(s). In some embodiments, the microfluidic, electrochemical device further comprises a second electrode assembly comprising a second substrate layer which supports one or more electrode(s). In some embodiments, the first or second electrode assembly further comprises a barrier material surrounding at least a portion of the electrode. In some embodiments, the electrode is substantially surrounded by the barrier material. In some embodiments, the first or second substrate layer has a two-layer structure comprising a paper or plastic-film and a layer of the barrier material. In some specific embodiments, the barrier material comprises polymerized photoresist disposed on the supporting layer and substantially surrounding the electrode. In other specific embodiments, the barrier material comprises a fluid-impermeable sheet having apertures of a dimension for receiving the electrode. The fluid-impermeable sheet is positioned over the first or second substrate layer and substantially surrounds the electrode. In some specific embodiments, the fluid-impermeable sheet comprises double-sided adhesive tape. In other embodiments, the first or second substrate layer are integral with and form a unitary body with the barrier material. The barrier material provides a barrier to fluid flow and can prevent malfunction of the electrochemical device, for example, by short circuiting the electrodes.

The first porous, hydrophilic layer overlays with the electrode assembly, wherein the hydrophilic layer comprising a fluid-impermeable barrier that substantially permeates the thickness of the hydrophilic layer and defines a boundary of one or more hydrophilic channels within the hydrophilic layer, wherein the one or more hydrophilic channels comprise a first hydrophilic region which is in fluidic communication with the one or more electrodes.

Figure 1:
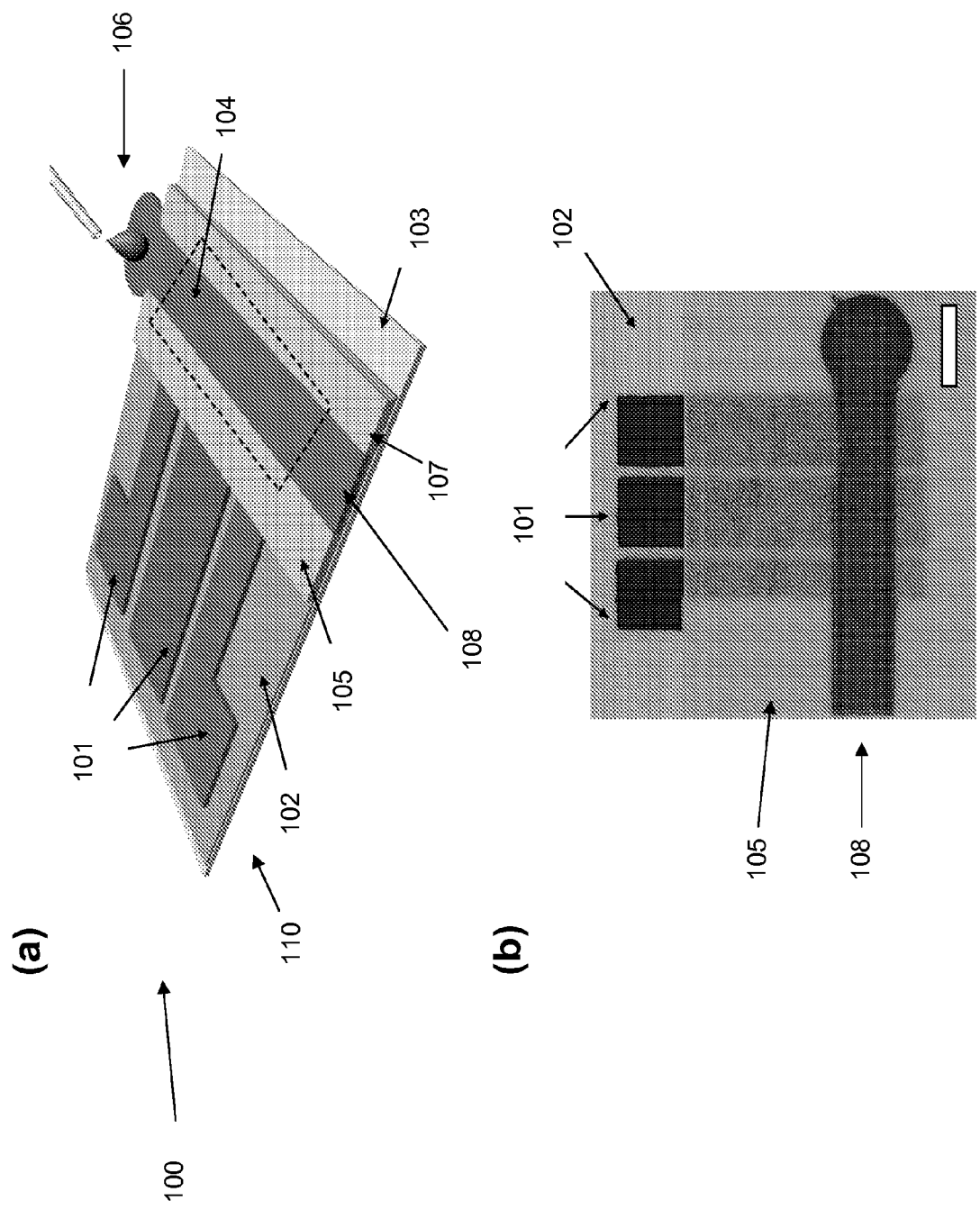
FIG. 1 is an illustration of a microfluidic, electrochemical device fabricated by stacking a substrate layer with electrodes, a fluid-impermeable layer, and a layer of patterned porous, hydrophilic layer comprising a first hydrophilic region.

In one aspect, a microfluidic, electrochemical device disclosed herein is described with reference to FIG. 1 and demonstrates the general principles of the device. FIG. 1(a) schematically illustrates a perspective view of a microfluidic, electrochemical device 100, which includes an elecrode assembly 110 and and a patterned porous, hydrophilic layer 107. The electrode assembly 110 comprises a substrate layer 103 supporting electrodes 101. The electrode further comprises a barrier material 102 disposed between electrodes 101. In some embodiments, the barrier material 102 surrounds at least a portion of the electrodes 101. In some embodiments, the electrodes 101 is substantially surrounded by the barrier material 102. In some specific embodiments, the barrier material 102 comprises polymerized photoresist disposed on the supporting layer 103 and substantially surrounding the electrodes 101. In other specific embodiments, the barrier material 102 comprises a fluid-impermeable sheet having apertures of a dimension for receiving the electrode. In some specific embodiments, barrier material 102 comprises double-sided adhesive tape. The patterned porous, hydrophilic layer 107 comprises a fluid-impermeable barrier 105 that substantially permeates the thickness of the patterned porous, hydrophilic layer and defines a boundary of a hydrophilic channel 108. The hydrophilic channel 108 comprises a first hydrophilic region 104, which is in fluidic communication with electrodes 101. In some embodiments, the microfluidic, electrochemical device further comprises an applicator region 106, which is in fluidic communication with the first hydrophilic region 104. Once a fluidic sample is deposited in the depositing region 106, the fluid will wick into the hydrophilic channel 108 though capillary mechanism. Once the sample reaches the first hydrophilic region 104, the analyte of the sample contacts the electrodes disposed below the hydrophilic region to create an electrochemical cell. An electrochemical signal can be measured via electrochemical reactions conducted though electrodes 101. FIG. 1(b) illustrates a photograph of a top view of the microfluidic, electrochemical device 100.

Figure 3:
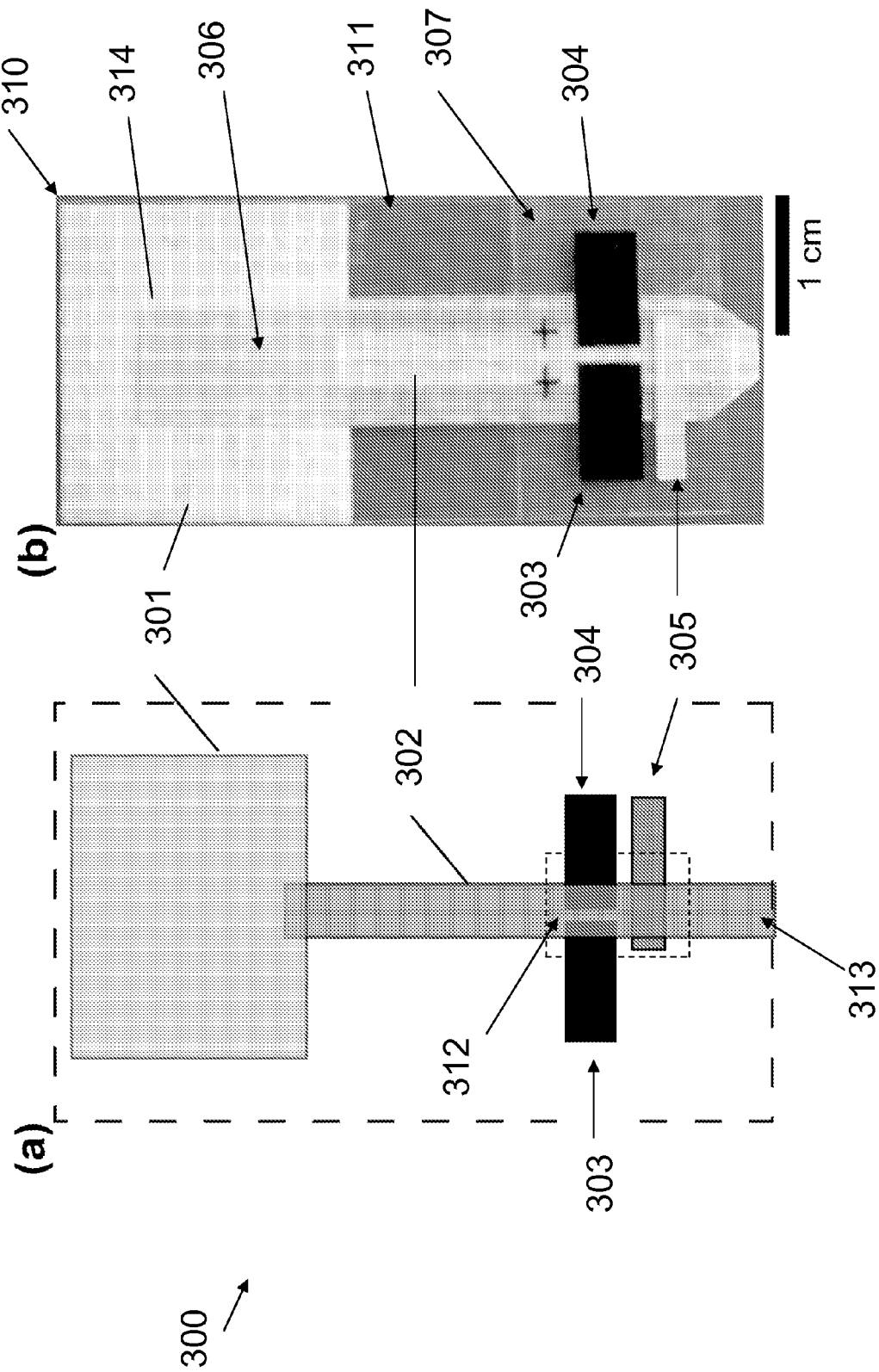
FIG. 3 is an illustration of a microfluidic, electrochemical device fabricated by stacking a substrate layer with electrodes, a fluid-impermeable layer, a layer of patterned porous, hydrophilic layer comprising a first hydrophilic region, and a fluid sink.

The substrate layer 103 on which the electrode(s) 101 are constructed can be a porous, hydrophilic layer or a plastic layer. In some embodiments, the substrate layer is paper. In other embodiments, the substrate layer is a plastic film. In some other embodiments, the substrate layer 103 is integral with and form a unitary body with the barrier material 102. By way of example, the substrate can be plastic, in which channels are etched to provide a depression in which the electrode is formed. Electrodes can be located as needed or desired on the substrate. By way of example, the electrodes can be aligned side by side (as shown in FIG. 1) or head to head (as shown in FIG. 3). Other electrode arrangements are contemplated.

Electrode(s) are fabricated using the methods and materials known in the art. Non-limiting examples of electro-conductive material suitable for electrode construction on the substrate layer include carbon ink, silver ink, Ag/AgCl ink, Copper, Nickel, Tin, Gold, or Platinum. In some embodiments, carbon ink is used for constructing the electrode on the substrate layer. In other embodiments, Ag/AgCl ink is used for constructing the electrode on the substrate layer. In yet other embodiments, gold is used for constructing the electrode on the substrate layer. In some specific embodiments, carbon ink is screen-printed on a layer of paper as the substrate layer. In other specific embodiments, carbon ink is screen-printed on a layer of polyester film as the substrate layer. In other specific embodiments, carbon ink is screen-printed on a layer of polyester film as the substrate layer. In yet other specific embodiments, Ag/AgCl ink is screen-printed on a layer of paper as the substrate layer. In yet other specific embodiments, Ag/AgCl ink is screen-printed on a layer of polyester film as the substrate layer.

Porous, hydrophilic layers that can be used in microfluidic, electrochemical devices described herein include any hydrophilic layer that wicks fluids by capillary action. In one or more embodiments, the porous, hydrophilic layer is paper. Non-limiting examples of porous, hydrophilic layers include chromatographic paper, filter paper, nitrocellulose and cellulose acetate, cellulosic paper, filter paper, paper towels, toilet paper, tissue paper, notebook paper, KimWipes, VWR Light-Duty Tissue Wipers, Technicloth Wipers, newspaper, any other paper that does not include binders, cloth, and porous polymer film. In general, any paper that is compatible with the selected patterning method may be used. In certain embodiments, porous, hydrophilic layers include Whatman chromatography paper No. 1.

In one or more embodiments, the hydrophilic layer is patterned following the procedures described in, e.g., WO 2008/049083 and WO 2009/121037. In certain embodiments, the hydrophilic paper is soaked in photoresist, and photolithography is used to pattern the photoresist to form the barriers following the procedures described in WO 2008/049083. The photoresist used for patterning porous, hydrophilic material include SU-8 photoresist, SC photoresist (Fuji Film), poly (methylmethacrylate), nearly all acrylates, polystyrene, polyethylene, polyvinylchloride, and any photopolymerizable monomer that forms a hydrophobic polymer.

Other hydrophilic material such as nitrocellulose and cellulose acetate are commonly used and well-known membranes for their use in fluid diagnostics, but are not compatible with solvents typically used in photolithography. In some other embodiments, the patterned hydrophilic paper is fabricated using method illustrated in copending PCT Application, titled "Methods Of Micropatterning Paper-Based Microfluidics," filed on Mar. 8, 2010, Publication No. WO 2010/102294, which is incorporated by reference. Other methods, such as screening, stamping or printing, are suitable for patterning such materials. In addition, the hydrophilic layer and the fluid-impermeable barrier regions could be prepared using materials that are compatible with the testing conditions, e.g., temperature, pH, and/or ionic strength.

After the patterning process, the resulting patterned porous, hydrophilic layer contains one or more defined hydrophilic channels which allows the microfluidic flows by capillary action.

Fabrication of the Microfluidic, Electrochemical Device

In some embodiments, the electrode assembly includes a barrier material and paper or plastic film. In one exemplary method, a microfluidic, electrochemical device is fabricated by first making a stencil using a fluid-impermeable layer. The stencil made from the fluid-impermeable layer can be made using any methods commonly known in the art. In some embodiments, the stencil is designed by a computer software and then cut by a laser cutter. In some embodiments, the stencil is made from a double-sided type and designed by computer software such as Adobe Freehand®. The stencil is then cut into designed configuration by using a laser cutter. The stencil is then attached to a substrate layer with predetermined areas of the substrate layer exposed. The exposed areas define the location of the electrodes of the electrode assembly.

The stencil can serve as a filler material between electrodes and can also provide a barrier to fluid flow into the gap between electrodes which could impede the measurement process. In one or more embodiments, the stencil is prepared from a fluid-impermeable material such as a plastic sheet. In certain embodiments, the fluid-impermeable layer is an adhesive sheet or tape. Non-limiting examples of fluid-impermeable layer includes Scotch® double-sided carpet tape, water-impermeable barriers include 3M Double Sided Tape, Tapeworks double sided tape, CR Laurence black double sided tape, 3M Scotch Foam Mounting double-sided tape, 3M Scotch double-sided tape (clear), QuickSeam splice tape, double sided seam tape, 3M exterior weather-resistant double-sided tape, CR Laurence CRL clear double-sided PVC tape, Pure Style Girlfriends Stay-Put Double Sided Fashion Tape, Duck Duck Double-sided Duct Tape, and Electriduct Double-Sided Tape.

In some embodiments, one or more electrodes are then constructed on the exposed areas of the substrate layer. In some specific embodiments, the electro-conductive material is screen-printed onto the exposed areas of the substrate layer to form the electrode. In some embodiments, the electrode(s) are screen-printed on the substrate layer. In other embodiments, other methods of constructing the electrodes on the substrate layer can be used. Non-limiting examples of constructing the electrodes on the substrate layer include metal deposition (such as sputtering and sputter deposition, vapor deposition, thermal spray coating, and ion beam techniques), electrodeposition coating, etching, and self-assembly. In some other embodiments, the conductive ink is used to filled the opening of the stencil. Optionally, the substrate layer can be submitted to heating facilitate the drying of the ink. Subsequently, the protective layer of the double-sided type can be removed and a patterned porous, hydrophilic layer containing a first hydrophilic region can be attached onto the double-sided type in a way to allow the first hydrophilic region to contact at least a portion of the electrode.

In other embodiments, the substrate layer are integral with and form a unitary body with the barrier material. Non-limiting examples of fabricating such substrate layer include etching a film comprising a plastic material or other material suitable for the etching method to form channels to provide a depression in which the electrode is formed.

Configuration of the Electrodes

In some embodiments, the electrodes comprise a working electrode, an reference electrode, and a counter electrode. FIG. 1 demonstrates an arrangement of the electrodes where all three electrodes are side by side to each other in a single electrode assembly. Such electrode arrangement can be referred to as the side-by-side arrangement ("S-S").

Figure 2:
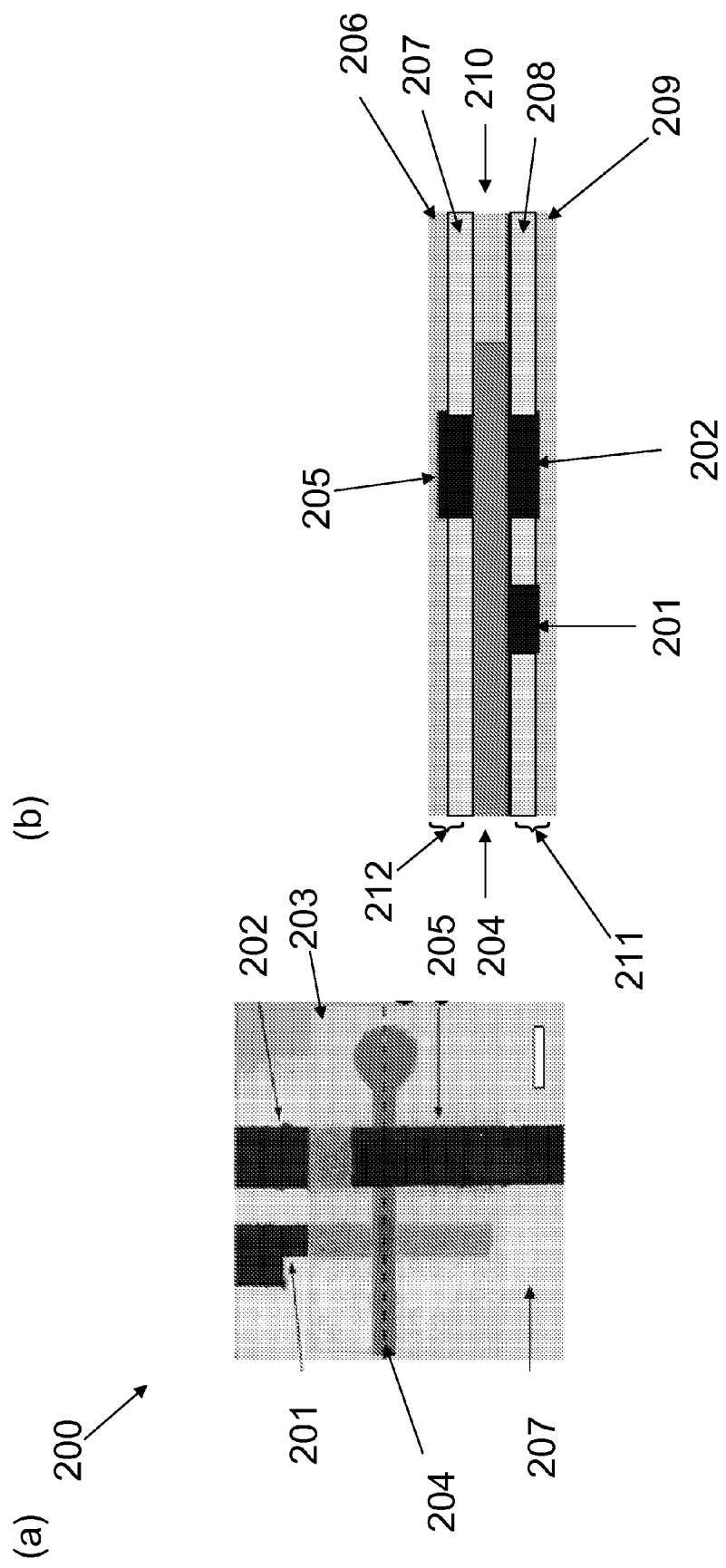
FIG. 2 is an illustration of a three-dimensional microfluidic device fabricated by stacking a first substrate layer with electrode(s), a first fluid-impermeable layer, a layer of patterned porous, hydrophilic layer comprising a first hydrophilic region, a second fluid-impermeable layer, and a second substrate layer with electrode(s)

FIG. 2 illustrates a microfluidic, electrochemical device 200 with a arrangement of the electrodes where the working electrode and the counter electrode are placed in a face-to-face manner ("F-F"). The microfluidic, electrochemical device 200 is constructed using any of the methods described herein. FIG. 2(b) illustrates a cross-sectional side view of the device. As FIG. 2(b) illustrates an electrode assembly 211 with a two-layer structure comprising a reference electrode 201, a working electrode 202, a substrate layer 209, e.g., a polyester layer or a paper layer 209, on which the electrodes are disposed and a barrier material 208 located at least between the reference electrode 201 and working electrode 202. In some embodiments, the barrier material comprises a fluid-impermeable sheet 208 having apertures of a dimension for receiving the electrode, where the fluid-impermeable sheet is disposed over the substrate layer and substantially surrounding the electrode. Non-limiting examples of the fluid-impermeable sheet include double-sided adhesive tape. FIG. 2(b) also illustrates a second electrode assembly 212 comprising a second substrate layer 206 supporting a counter electrode 205. Barrier material 207 surrounds the electrode 205. A patterned hydrophilic layer 210 is disposed between the upper electrode assembly 212 housing counter electrode 205 and the lower electrode assembly 210 housing working electrode 202 and reference electrode 201. Hydrophilic layer 212 includes a hydrophilic channel 204 and a hydrophobic barrier region 203. The substrate layer 206 containing the counter electrode 205 is attached to one side of the hydrophilic layer 210 via a stencil fluid-impermeable layer 207. The substrate layer 209 containing the reference electrode 201 and working electrode 202 is attached to the other side of the hydrophilic layer 210 via a stencil hydrophobic impermeable layer 208. The device is constructed in a way such that counter electrode 205 and working electrode 202 are facing each other. Such an arrangement of electrode is referred to as the face-to-face arrangement ("F-F"). Without being bound to any specific theory, it is believed that the F-F configuration will have a higher effective surface area for electrochemical reactions to take place than the S-S configuration, since the electrochemical reactions take place between the faces of the two electrodes. In comparison, the S-S configuration will allow smaller effective surface area. A top view of the F-F device 200 is shown in FIG. 2(a), which demonstrates that the counter electrode 205 and working electrode 202 are facing each other resulting in a large electrochemical reaction surface area.

In some other embodiments, the first or second substrate layer are integral with and form a unitary body with the barrier material. Accordingly, barrier material 209 and substrate layer 208 form a unitary body. In some other embodiments, similarly, barrier material 207 and substrate layer 206 form a unitary body.

Microfluidic, Electrochemical Device with a Fluid Sink

In some embodiments, a microfluidic, electrochemical device with a fluid sink is described. The fluid sink is in fluidic communication with one end of the hydrophilic channel comprising the first hydrophilic region within the patterned porous, hydrophilic layer and functions as a sink to allow the fluidic sample to continuously flow through the first hydrophilic region and pass across the electrodes. Without being bound to any specific theory, it is believed that the continuous fluidic flow passing the electrodes can result in higher volume of sample contacting the surface of the electrodes, thus resulting a microfluidic, electrochemical device with a higher sensitivity and reproducibility. The fluid sink includes any hydrophilic layer that wicks fluids by capillary action. The fluid sink can be any of the material used for the porous, hydrophilic layers described herein. In one or more embodiments, the fluid sink is a hydrophilic channels or regions within the patterned porous, hydrophilic layer. In other embodiments, the fluid sink is paper. In other embodiments, the fluid sink is a pad of cellulose blotting paper.

A microfluidic, electrochemical device 300 with a fluid sink 301 is described with reference to FIG. 3. FIG. 3(a) demonstrates a simplified schematic view of the device 300. Reference electrode 305, counter electrode 303, and working electrode 304 are in contact and fluidic communication with a first hydrophilic region 312 within the hydrophilic channel 302. The hydrophilic channel 302 is in fluidic communication with an absorbing pad 301. During use, after a fluidic sample is deposited at the bottom area 313 of the hydrophilic channel 302, the fluid will continuously wick into the absorbing pad 301, thus generating a large volume of fluidic flow though the electrodes 303, 304, and 305. FIG. 3(b) shows a photographic view of a microfluidic, electrochemical device 300 with a fluid sink substrate 301. The patterned hydrophilic layer 314 comprises the hydrophilic channel 302 and a barrier region 306. The three electrodes 303, 304, and 305 are constructed on a substrate layer (omitted for simplification) and are attached to the patterned hydrophilic layer 314 using an adhesive fluid-impermeable layer 307. The fluid sink 301 is within a layer 310 beneath the hydrophilic layer 314. The layer 310 also comprises a hydrophobic region 311. In some embodiments, the layer 310 can also be a patterned hydrophilic layer and the fluid sink 301 is one of the hydrophilic channels or regions within the layer 311 and area 311 comprises the hydrophobic substrate described herein.

Three-Dimensional Microfluidic, Electrochemical Device with Vertical Fluidic Flow In some embodiments, the microfluidic, electrochemical device is three-dimensional which allows vertical fluidic flow in addition to the two-dimensional fluidic flow within the patterned porous, hydrophilic layer. The three-dimensional microfluidic, electrochemical device comprise alternated patterned porous, hydrophilic layer and fluid-impermeable layers in addition to the substrate with the electrode(s) attached. The fluid-impermeable layers comprise apertures and the microfluidic device relies on those apertures to direct vertical microfluidic flow in which channels are etched to provide a depression in which the electrode is formed. The fluid-impermeable layer can be a sheet that is not soluble in the fluid analyzed by the microfluidic, electrochemical device and that provides the desired level of device stability and flexibility. The fluid-impermeable layer can comprise one or more openings which are in alignment with at least of a portion of the defined hydrophilic channels within the patterned porous, hydrophilic layer. When disposed between the substrate layer with the electrode(s) and patterned porous, hydrophilic layer containing the first hydrophilic region, the opening within the fluid-impermeable layer will be in alignment with both portions of the electrodes and the first hydrophilic region. Thus, upon deposition of a fluidic sample, the fluid flows through the hydrophilic channels to reach the first hydrophilic region, resulting in its contact with the electrodes and enabling appropriate electrochemical reactions.

In one or more embodiments, the fluid-impermeable layer is a plastic sheet. In certain embodiments, the fluid-impermeable layer is an adhesive sheet or tape. Non-limiting examples of fluid-impermeable layer includes Scotch® double-sided carpet tape, water-impermeable barriers include 3M Double Sided Tape, Tapeworks double sided tape, CR Laurence black double sided tape, 3M Scotch Foam Mounting double-sided tape, 3M Scotch double-sided tape (clear), QuickSeam splice tape, double sided seam tape, 3M exterior weather-resistant double-sided tape, CR Laurence CRL clear double-sided PVC tape, Pure Style Girlfriends Stay-Put Double Sided Fashion Tape, Duck Duck Double-sided Duct Tape, and Electriduct Double-Sided Tape. In certain specific embodiments, double-sided tape is used as the fluid-impermeable layer. Double-sided tape adheres to two adjacent layers of patterned paper and can bind to other components of the microfluidic, electrochemical device. It is impermeable to water, and isolates fluid streams separated by less than 200 μm. In addition, it is also sufficiently thin to allow adjacent layers of porous, hydrophilic layers to contact through openings of the tape. It can easily separate from the paper to which it adheres and thus allow disassembly of stacked devices and it is inexpensive and widely available.

As an alternative to double-sided tape, a heat-activated adhesive can be used to seal the fluid-carrying layers together. Indeed, any fluid-impermeable material that can be shaped and adhered to the pattern hydrophilic layers can be used. In addition, it is also possible to use the same material that is used to pattern the paper layers to join the layers of paper together. In one or more embodiments, a layer of photoresist is disposed between two adjacent patterned porous, hydrophilic layers.

Figure 4:
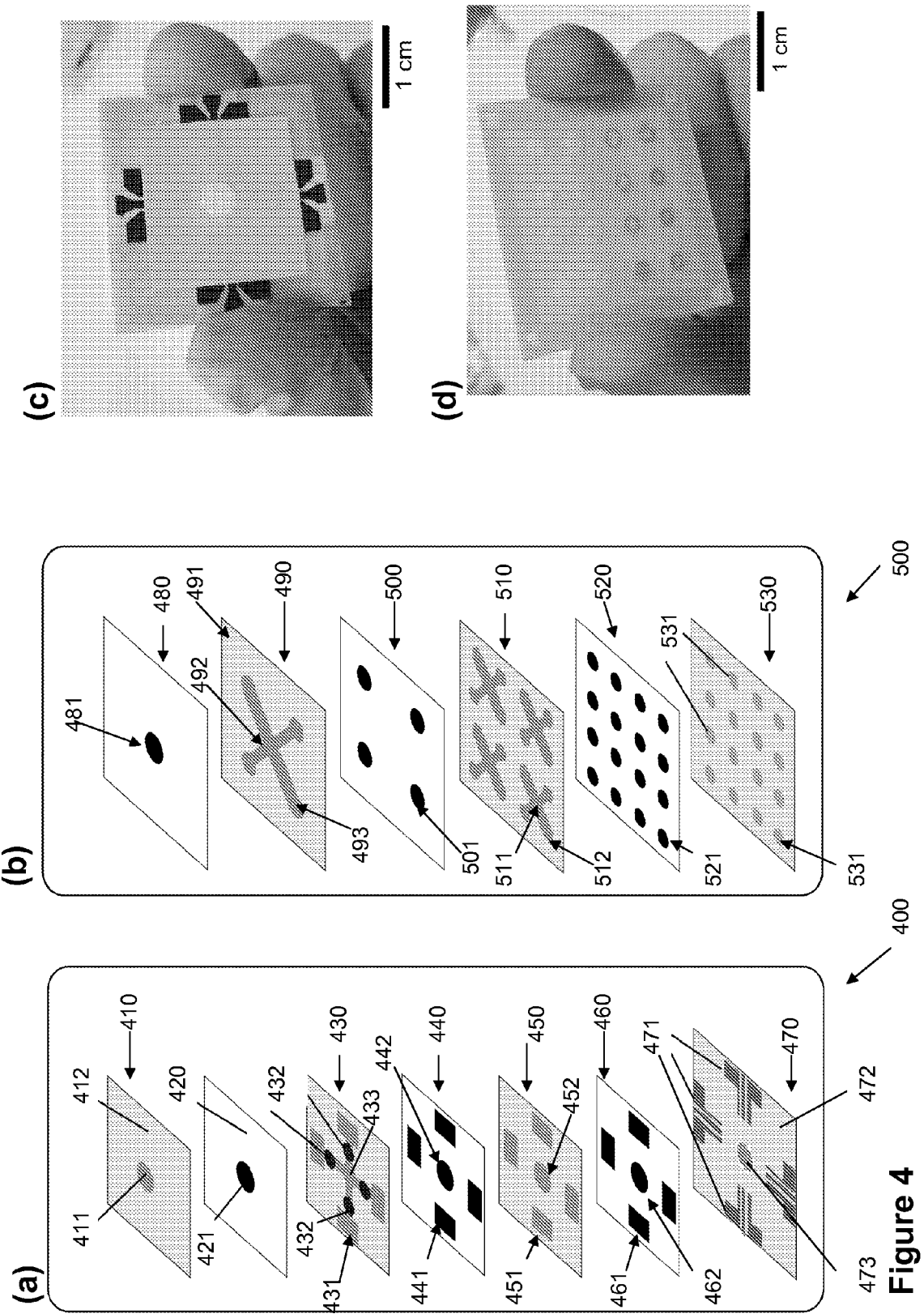
FIGS. 4(a) and 4(c) are illustrations of a microfluidic, electrochemical device fabricated by stacking a substrate layer with electrodes and multiple layers of patterned porous, hydrophilic layers with a fluid-impermeable layer disposed between every two adjacent patterned porous, hydrophilic layers and between the adjacent substrate layer and the patterned porous, hydrophilic layer.
FIGS. 4(b) and 4(d) are illustrations of a microfluidic device fabricated by stacking multiple layers of patterned porous, hydrophilic layers with a fluid-impermeable layer disposed between every two adjacent patterned porous, hydrophilic layers.

The three-dimensional microfluidic device is described with reference to FIG. 4. FIG. 4(a) illustrates a three-dimensional microfluidic, electrochemical device 400 assembled using patterned porous, hydrophilic layers 410, 430, 450, fluid-impermeable layers 420, 440, 460, and the substrate layer 470 with electrodes 471 attached. In some embodiments, the patterned hydrophilic layers comprises paper which comprises hydrophilic channels or regions defined by the hydrophobic barrier such as photo resist on the paper. In some embodiments, the fluid-impermeable layers comprise double-sided types which has apertures to direct fluidic flow. As illustrated in FIG. 4(a), the first hydrophilic paper layer 410 comprises a hydrophilic region 411 and hydrophobic area 412 formed by photo resist. Once a fluidic sample is deposited in hydrophilic region 411, the fluid can flow though the double-side tape layer 420 via aperture 421 and into the center of the hydrophilic channel 433 within the second patterned hydrophilic paper layer 430. Through capillary actions, the fluid will then reach block-shaped hydrophilic regions 431. Optionally, at certain hydrophilic regions 432, a filtration agent or other reactant can be deposited to pre-treat the fluidic sample. Other non-limiting examples of assay reagents include other protein assay reagents, other glucose assay reagents, sodium acetoacetate assay reagents, sodium nitrite assay reagents, or a combination thereof. Other suitable assay reagents will be apparent to one skilled in the art.

Once reaching the hydrophilic region 431, the fluidic sample can then flow through apertures 441 on double-sided tape layer 440 and into the first hydrophilic region 451, which is in fluidic communication with electrode 471 on substrate 470, through aperture 461 of tape layer 460. Part of the deposited fluidic sample will also reach hydrophilic region 473 on the substrate layer 470 by sequentially passing through aperture 442, hydrophilic region 452, and aperture 462.

In some other embodiments, a three-dimensional microfluidic device 500 for running colorimetric assay is described with reference to FIG. 4(b). The device is assembled by alternated layers of double-sided tape 480, 500, 520 and patterned paper 490, 510, and 530. When a fluidic sample is deposited in aperture 481 of tape layer 480, the fluid will flow into the center region of the cross-shaped hydrophilic channel 492 on patterned paper layer 490 defined by photo resist 491, and reach the edge of the hydrophilic channel 493. In turn, the fluid will flow through the aperture 501 of the double-sided tape layer 500 and into the smaller cross-shaped hydrophilic channel 511 on patterned paper layer 500. The flow of the fluid then reaches the edge of the hydrophilic channel 512, pass through aperture 521 of tape layer 520, and reaches the hydrophilic regions 531 on the bottom patterned hydrophilic layer 530. Regions 531 are test zones pre-spotted with reagents for one or more colorimetric assays. A more detailed description of the three-dimensional microfluidic device for running colorimetric assay can be found in WO 2009/121037, filed Mar. 27, 2009, which is hereby incorporated by reference in its entirety.

The incorporation of multiple detection methods on a single three-dimensional microfluidic device has multiple advantages: i) it extends the range of analytes that the device is able to be detected; ii) it improves the reliability of the diagnosis; iii) it has the ability to quantitatively detect multiple analytes with optimal selection of the detection method for each; iv) it allows the integration of high density sensors; v) it lowers the cost of each detection, since it shares the cost of sample preparation, introduction, and microfluidic distribution systems over multiple assays.

The microfluidic device can use apertures or openings within the separating fluid-impermeable layer to direct vertical microfluidic flow. In some embodiments, the aperture or opening within the fluid-impermeable layer is filled with a hydrophilic medium to improve the vertical flow (or flow through). The hydrophilic medium fills the opening within the separating layer to bridge the gap between the adjacent hydrophilic layers. As a result, the two microfluidic regions within two adjacent patterned porous, hydrophilic layers that partially overlap with the opening will be in direct contact with the hydrophilic material in the opening, thus allowing optimized microfluidic flow by capillarity. In one or more embodiments, the porous, hydrophilic material substantially fills the void within the separating layer created by the aperture. In one or more embodiments, the porous, hydrophilic material substantially matches the shape of the opening. The porous, hydrophilic material filling the opening can be, for example, porous paper pads or "dots" that have a thickness similar to the thickness of the fluid-impermeable layer. The paper can be cut into shape to match the dimensions of the void space created by the aperture in the fluid-impermeable layer.

Other materials as described herein suitable for use as the patterned porous, hydrophilic layer and the fluid-impermeable layer are also contemplated.

Detection Methods for Electrochemical Analysis Using the Microfluidic, Electrochemical Devices In some embodiments, a fluidic sample is deposited in one of the one or more hydrophilic channels to allow the fluid sample to flow through the hydrophilic channel to contact with the electrode. In some embodiments, the fluidic sample can be deposited on top of the electrode. In some other embodiment, the fluidic sample is deposited in one end of a hydrophilic channel and is wicked through the channel to contact the electrode. In some embodiments, the fluidic sample is deposited on one end of the hydrophilic channel comprising the first hydrophilic region and the microfluidic, electrochemical device further comprises a fluid sink in fluidic communication with the other end of the hydrophilic channel comprising the first hydrophilic region to maintain a constant fluidic low of the fluidic sample through the electrode(s).

The electrochemical devices can be configured to be used in a variety of analytical methods. Non-limiting methods include impedance measurement, amperometry (measurement of electrical currents), biamperometry, stripping voltammetry, differential pulse voltammetry, cyclic voltammetry, coulometry, and potentiometry. In some embodiments, the analytes within the fluidic sample are detected by chronoamperometric method. In some specific embodiments, the analyte is glucose. Other non-limiting examples of analyte which can be detected by chronoamperometric method include metabolites such as cholesterol, uric acid, and lactate, blood gases such as oxygen, DNA, and other analytes such as haemoglobin, nitric oxide, and blood ketones.

In some embodiments, the glucose in the sample is detected using the microfluidic, electrochemical devices by chronoamperometric method. Chronoamperometry is an electrochemical technique in which the potential of the working electrode is stepped, and the resulting current from faradic processes occurring at the electrode (caused by the potential step) is monitored as a function of time. Information about the identity of the electrolyzed species can be obtained from the ratio of the peak oxidation current versus the peak reduction current. The reactions for the glucose detection are

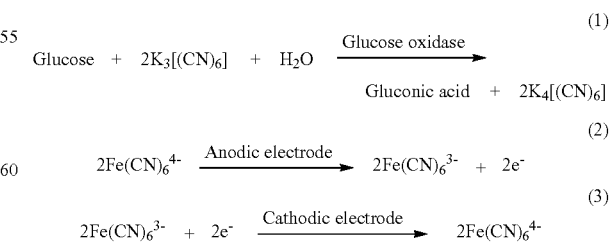

In the first step, glucose oxidase catalyzed the oxidation of glucose to gluconic acid with concomitant reduction of Fe(III) to Fe(II) (eq 1); the Fe(CN)$_6^{4-}$ ions generated were detected chronoamperometrically (eq 2). The corresponding cathodic reaction was described in (eq 3).

In some embodiments, the detection of glucose using microfluidic, electrochemical device demonstrate comparable sensitivity and detection limits compared with the detection used in bulk solutions. The microfluidic, electrochemical device, however, several advantages: i) it stabilizes the geometry of the electrode; ii) it reduces the effect of convection of liquids due to random motion, vibration and heating; iii) it minimizes the total volume of solution required for analysis.

Without wishing to be bound to any particular theory, it is believed that the use of microfluidic, electrochemical device confines the fluids in the hydrophilic channel, inhibits the convective movement of fluids, and thus facilitates the chronoamperometric measurements by minimizing the disturbances of the stationary boundary layer in the vicinity of electrodes due to vibration, thermal or density-based convection, and other disturbing sources. In addition, the normal level of glucose in urine is 0.1-0.8 mM, and 3.5-5.3 mM in whole blood. In some embodiments, the detection limit of glucose in the microfluidic, electrochemical device is about 0.22 mM (corresponding to 4 mg/mL). This value is below the approximately 1.0 mM claimed in specifications of conventional glucometers.

In other embodiments, the analytes within the fluidic sample is detected and measured by anodic stripping voltammetry (ASV) through the use of the microfluidic, electrochemical device described herein. Anodic stripping voltammetry is a voltammetric method for quantitative determination of specific ionic species. The analyte of interest is electroplated on the working electrode during a deposition step, and oxidized from the electrode during the stripping step. The current is measured during the stripping step. In some specific embodiments, heavy metal ions in a fluidic sample can be detected by anodic stripping voltammetry thought the use of the microfluidic, electrochemical device. Non-limiting examples of heavy metal ions include mercury, lead, copper, zinc, bismuth, and cadmium.

The pollution of heavy-metal ions in soil and water presents a global issue, and poses a severe threat to both the ecosystem and humans. Square-wave anodic stripping voltammetry (SWASV) is an ASV method frequently used for the measurement of trace heavy metals because it greatly reduces the background noise coming from the charging current during the potential scan. Conventional ASV measurements of heavy metal ions are usually performed either by dipping electrodes in a sample solution under controlled stirring condition or by placing a sample droplet onto the electrodes. The former approach is not practical in field measurements due to the difficulty of synchronizing the stirring and ASV procedures. The latter one shows limited sensitivity of measurement because pre-accumulation of analytes in stripping is limited by diffusion. Additionally, in this case, new electrodes are usually required for each measurement since it is difficult to remove the residue of deposited metals in a stagnant drop of solution before the next cycle of ASV.

In some embodiments, heavy metal ions are detected by anodic stripping voltammetry (ASV) through the use of the microfluidic, electrochemical device described herein. In some specific embodiments, Pb(II) is detected by the use of the microfluidic, electrochemical device described herein. In some embodiments, a fluid sink is included in the microfluidic, electrochemical devices. In some specific embodiments, the fluid sink is a pad of cellulose blotting paper as a sink in the outlet of the hydrophilic channel (see FIG. 3). The use of an absorbing pad allows the continuous wicking of fluids to pass across the electrodes, and facilitates the plating of metals, as well as the cleaning of electrodes. In some embodiments, the size of the cellulose blotting paper is adjusted to optimize the wicking time of fluids in the hydrophilic channel so that the flow stopped before the system entered the equilibration step in the process of SWASV, which results in higher sensitivity and reproducibility of the measurement. Without wishing to be bound to any particular theory, it is believed that the enhanced sensitivity can be attributed to the high efficiency of the accumulation of metals on the electrodes by convection of flowing fluids in the porous, hydrophilic channels over the electrodes, and to the large volume (~800 µL) of sample that flows across the surface of the electrodes.

The following example is provided to illustrate the invention, which is not intended to be limiting of the invention, the scope of which is set forth in the claims which follow.

Chemical Reagents

Carbon ink (E3456) and Ag/AgCl ink (AGCL-675C) were purchased from Ercon Inc (Wareham, Mass.) and Conductive Compound (Hudson, N.H.), respectively. Glucose oxidase (136,300 U/mg, *Aspergillus niger*), glucose, and potassium ferricyanide were purchased from Aldrich and used as received. Stock solutions of β-D-glucose were prepared in a PBS buffer (pH 7.0) and allowed to mutarotate overnight before use. Atomic absorption standard solutions of Pb(II) ($10^4$ mg/L), Zn(II) ($10^3$ mg/L), and Bismuth(III) ($10^3$ mg/L) were obtained from Aldrich, USA, and diluted as required. 0.1M acetate buffer (pH 4.5) was used as a supporting electrolyte.

Apparatus

All chronoamperometric measurements were performed with a bipotentiostat (PINE Instrument Company, Model AFCBP1). A modular electrochemical system AUTOLAB equipped with PGSTAT12 was used in combination with GPES software (Eco Chemie) for the anodic stripping voltammetric measurements of heavy metal ions.

Fabrication of the Devices

Electrodes

A microfludic paper-based elecrochemical device (µPEDs) was fabricated by screen-printing carbon ink (or Ag/AgCl ink for a reference electrode) on a piece of paper or polyester film. A stencil was generated for printing by designing patterns of electrodes using Adobe Freehand®, followed by cutting the pattern into double-sided adhesive tape using a laser-cutter (VersaLASER VLS3.50, Universal Laser Systems Inc.). The stencil was taped on top of a paper or plastic substrate, and filled the openings of the stencil with ink. The electrodes were baked on a hotplate at 100° C. for 30 minutes. After the ink dried, the protective backing layer of the tape was removed and the adhesive layer on the substrate for the assembly of a paper channel was left on the top of electrodes. The thickness of the electrodes was approximately 100 µm. A typical working and counter electrode had dimensions of 1.5 cm in length and 4 mm in width, and a typical reference electrode had dimensions of 1.5 cm in length and 3 mm in width.

Microfluidic Channels

The layers of patterned hydrophilic paper were constructed following the procedures described in WO 2008/049083. The patterns for the paper-based microfluidic devices were designed using the layout editor CleWin. Specifically, paper-based microfluidic channels were fabricated by patterning chromatography paper (Whatman 1 Chr) or polyester/cellulose blend paper (VWR® Spec-Wip) by photolithography or wax printing. Briefly, a piece of paper was soaked with SU-8 2010 photoresist, baked it at 95° C. for 5 min to remove solvents, and photoexposed it to UV light for 10 s through a photomask. The unpolymerized photoresist was removed by soaking the paper in acetone and washing three times with isopropanol. The polymers patterned on the paper form hydrophobic barriers to confine liquids in the microchannel. The paper microfluidic channel had dimensions of 4 mm in width and 100 μm in height (determined by the thickness of the paper), FIG. 1. The paper-based channels were assembled onto the electrodes using double-sided adhesive tapes. The contact area between a paper channel and a working electrode was 4 mm by 4 mm.

Chronoamperometric Measurements

Chronoamperometric experiments were performed using a 500 mV step potential (versus a carbon pseudo-reference electrode) to generate the calibration curve; these experiments used glucose with concentrations ranged from 0 to 22.2 mM (corresponding to 400 mg/dL). Solutions (Glucose oxidase 250 U/mL, $K_3[Fe(CN)_6]$ 600 mM, KCl 1.0 M in pH 7.0 PBS buffer) containing glucose with different concentrations were measured (each sample was examined eight times). The solution of enzyme was spotted on top of the paper microchannel. The solution of enzyme was distributed evenly in the paper channel due to the capillary wicking. After the solution dried, the enzyme was uniformly absorbed in the paper. When a solution of analytes was added into the microchannel, the solution distributed and mixed well with the pre-loaded enzyme. In another set of experiments, the enzyme solution was premixed with glucose samples before the chronoamperometric measurements. No obvious difference was observed between the two methods. Paper can also be easily modified to immobilize enzymes if necessary. All measurements were conducted at room temperature under ambient conditions. A carbon working electrode (on a plastic substrate) was used with a surface area of 16 $mm^2$ in contact with the fluid for the detection of glucose in the bulk solution. An average of the eight measurements of current readout was recorded and calculated the corresponding standard deviation.

Anodic Stripping Voltammetry

Stripping voltammetric measurements were performed by in situ deposition of the bismuth (500 μg/L) and the target metal ions with concentrations ranged from 0 to 100 ppb (μg/L). Non-deaerated solutions were used for all measurements, and each sample was measured eight times. All measurements were carried out using the square-wave anodic stripping voltammetry (SWASV) with a frequency of 20 Hz, a potential step of 5 mV, and an amplitude of 25 mV. SWASV experiments comprised an electrochemical deposition step at −1.2V for 120 s, an equilibration period of 30 s, and a square-wave voltammetric stripping scan usually from −1.2 to −0.5 V. Before each measurement a pre-conditioning step (for cleaning of the electrode) at a potential of +0.5V was applied for 60 s.

Square-wave anodic stripping voltammetry was used for the measurements of heavy metal ions in the μLPEDs. The measurements of trace metals relied on the simultaneous (in situ) plating of bismuth and target metals onto screen-printed carbon electrodes, which formed alloys followed by anodic stripping of metals from the electrode.

Electrochemical Characterization of Paper-Based Electrochemical Devices

Figure 5:
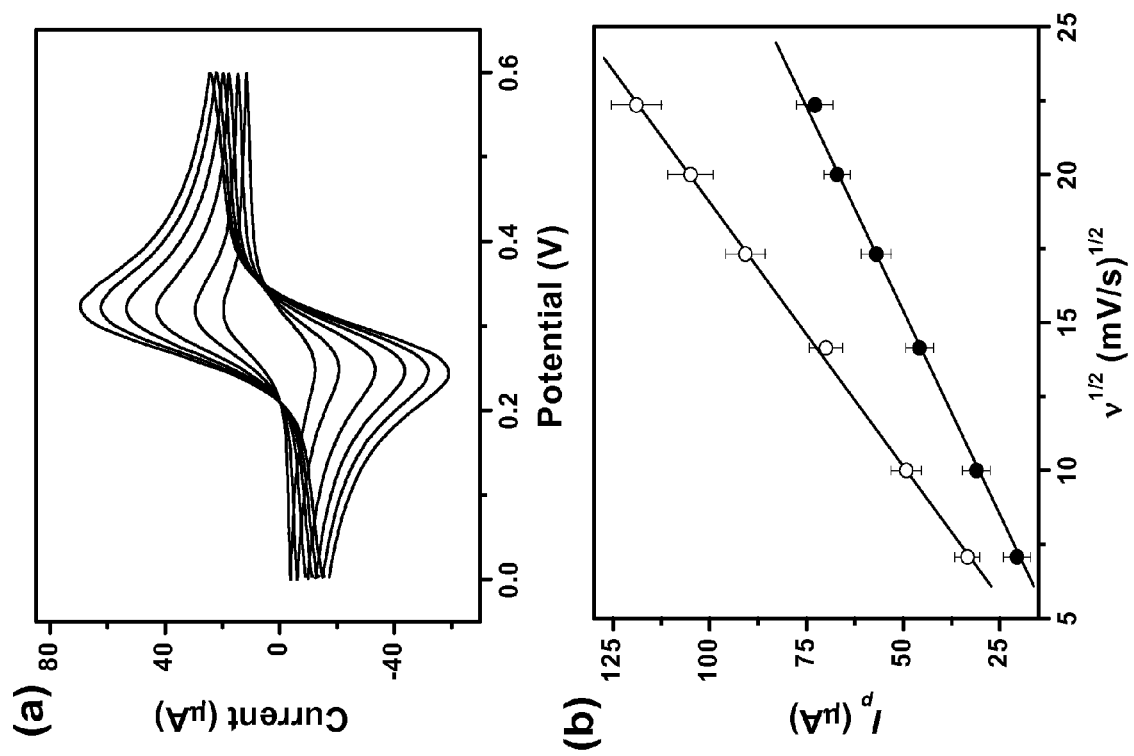
FIG. 5 (a) illustrates cyclic voltammograms of 2.0 mM ferrocene carboxylic acid in 0.5 M KCl aqueous solution (pH=7.0) in a µPED at various scan rates (ascending along y-axis): 50, 100, 200, 300, 400, and 500 mV/s; (b) illustrates the plot of anodic peak current versus the square root of the scan rate ($v^{1/2}$) for CV experiments conducted on a paper device (●) and in a bulk solution (○); the solid lines represent a linear fit to (●) with regression equation: y=−3.6+3.5× ($R^2$=0.998, n=8), and a linear fit to (○) with regression equation: y=−7.1+5.6×($R^2$=0.999, n=8)

Ferrocene carboxylic acid was used as a model redox-active compound to characterize electrochemical behavior of μPEDs (FIG. 5a). The peak shape of the CVs showed a typical reversible (Nernstian) electrochemical reaction in which the rate of reaction is governed by the diffusion of the electroactive species to the surface of a planar electrode. The difference in potential between the peaks of the reduction ($E_{pc}$) and oxidation ($E_{pa}$) curves was 0.068 V (a value that is close to the theoretical value of 0.059 V for the ferrocene redox pair) for all scan rates between 50 to 500 mV/s, and the peak current ratio ($i_{pa}/i_{pc}$) was equal to 1.0.[14] This reversible behavior indicated that no side reactions take place, and that, as expected, the kinetics of electron transfer was sufficiently rapid to maintain the surface concentrations of redox-active species at the values required by the Nernst equation.

FIG. 5b shows that the anodic peak current, $I_p$, was linearly proportional to the square root of the scan rate ($v^{1/2}$) in both bulk solution and the μPED. The value of diffusion coefficient evaluated by analyzing the slope observed in bulk solution was $4.3 \times 10^{-6}$ $cm^2$/sec, which was fairly close to the reported value of $5.7 \times 10^{-6}$ $cm^2$/sec. The current readout (FIG. 2b) measured using the paper device is about 30% lower than that measured in bulk solution. It was presumed that this difference was due to the fact that 30-40% of the volume in diffusional contact with the electrodes is occupied by the cellulose fiber of the paper. These results containing the redox-active species, did not slow the rate of mass-limited charge transfer relative to that in solution.

Chronoamperometric Analysis of Glucose in Urine

The use of a μPED in the analysis of glucose in artificial urine was demonstrated using chronoamperometry. Chronoamperometry offers a better signal-to-noise ratio than other electrochemical techniques in this kind of experiment, and the use of a thin slab of fluids mechanically clamped to the electrodes is more resistant to vibration than analysis in a larger volume of solution. The chronoamperometric measurement of current—reflecting charge transfer to/from the redox-active species as a function of time at constant applied voltages—begins with an initially large capacitive current. Upon the decay of the initial capacitive current within one to two seconds, Faradaic current (the current that is proportional to the concentration of the analyte) dominates. The current, I, decays as $t^{-1/2}$ as described by the Cottrell equation (eq 4) where n is the number of electrons, t is the $$i = \frac{nFAD^{\frac{1}{2}}C}{\pi^{\frac{1}{2}}t^{\frac{1}{2}}} \quad (4)$$

time, F is Faraday's constant, A is the area of the electrode, D is the diffusion coefficient of analytes, and C is the initial concentration of the reactants.

Figure 6:
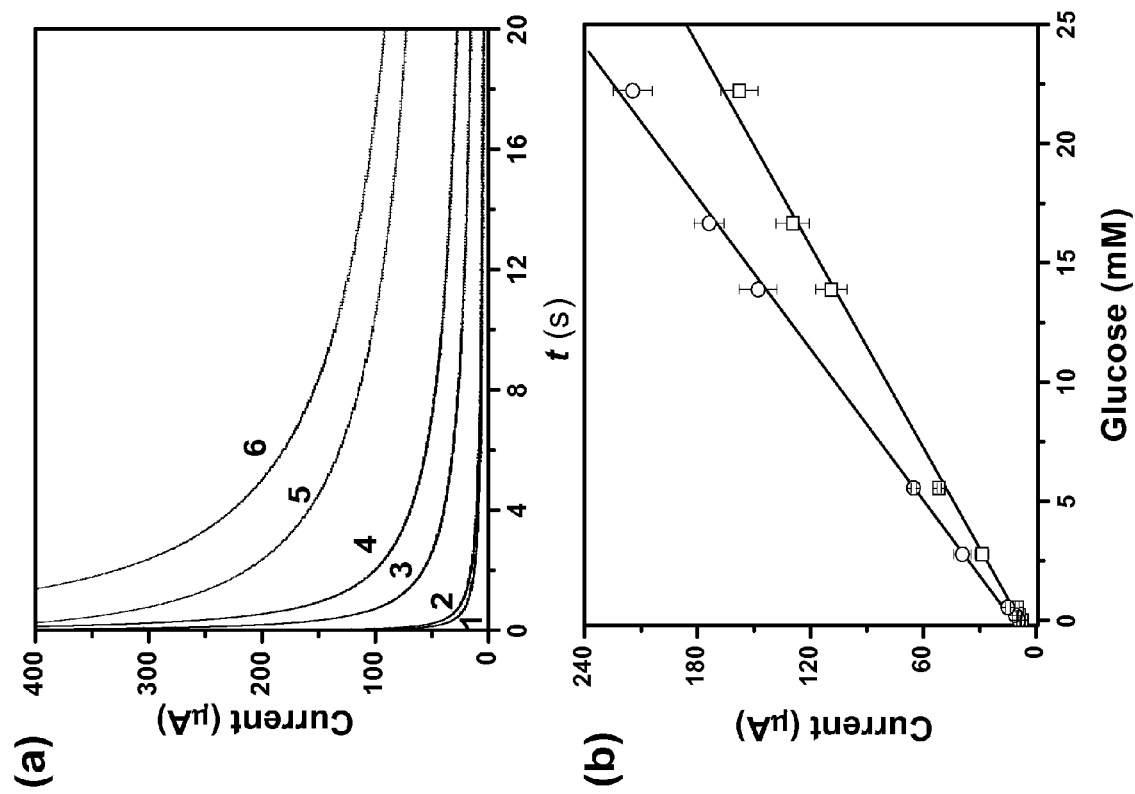
FIG. 6 (a) illustrates representative chronoamperometric curves for glucose concentrations (mM): 0 (1), 0.2 (2), 2.8 (3), 5.6 (4), 13.9 (5) and 22.2 (6) in the µPEDs; (b) illustrates calibration plots of current as a function of the concentration of glucose for the detection of glucose in the µPEDs (□) and in bulk solutions (○)

The μPED confines fluids in the paper channel, inhibits the convective movement of fluids, and thus facilitates the chronoamperometric measurements by minimizing the disturbances of the stationary boundary layer in the vicinity of electrodes due to vibration, thermal or density-based convection, and other disturbing sources. FIG. 6a shows a representative chronoamperometric response of the measurements of glucose using a μPED. Over the range of concentrations of glucose examined (0-22.2 mM), all the response curves reached a steady state two seconds after the step potential (also see the Cottrell plot in supplementary information). FIG. 6b shows a calibration curve for the detection of glucose. When the concentration of glucose was in the range of 0-22.2 mM, the current was linearly proportional to the glucose concentration in the artificial urine.

The interference of the sensing device with bovine serum albumin (BSA) as a typical globular protein; serum albumins are present in highest concentrations in serum, and thus relevant to bioanalysis. It was found that the presence of 40 μM BSA did not interfere with the measurement of glucose; this selectivity is due to the specificity of enzymatic oxidation of glucose; the BSA apparently does not foul the electrodes. Comparing the results of the detection of glucose in the μPEDs to those in bulk solutions (FIG. 6b), it was noticed that the two methods showed comparable sensitivity and detection limits; the paper matrix did not interfere with the detection. The paper matrix in the μPEDs has, however, several advantages: i) it stabilizes the geometry of the electrode; ii) it reduces the effect of convection of liquids due to random motion, vibration and heating; iii) it minimizes the total volume of solution required for analysis. The normal level of glucose in urine is 0.1-0.8 mM, and 3.5-5.3 mM in whole blood. The μPED device should therefore be capable of measuring glucose in other biological fluids such as serum and blood. The detection limit of glucose in the current μPED was about 0.22 mM (corresponding to 4 mg/mL). This value is below the approximately 1.0 mM claimed in specifications of conventional glucometers, and 0.5 mM obtained by colorimetric detection method reported previously. It was estimated the sensitivity of the glucose analysis to be 0.43 $\mu A \cdot mM^{-1} \cdot mm^{-2}$. In principle, other species in real urine and blood may interfere when, 500 mV potentials ae used for the analysis of glucose. The potential can be reduced to around 300 mV for the measurements in biological fluids, thanks to the enzymatic selectivity of glucose oxidase. The paper-based device also has the potential to be integrated with various separation techniques such as paper chromatography to minimize interferences.

Anodic Stripping Voltammetric Analysis of Heavy Metal Ions

Heavy-metal ions such as mercury, lead, and cadmium are toxic, non-biodegradable, and tend to accumulate in plants and animals. The pollution of heavy-metal ions in soil and water presents a global issue, and poses a severe threat to both the ecosystem and humans. Square-wave anodic stripping voltammetry (SWASV) is an ASV method frequently used for the measurement of trace heavy metals because it greatly reduces the background noise coming from the charging current during the potential scan. Conventional ASV measurements of heavy metal ions are usually performed either by dipping electrodes in a sample solution under controlled stirring condition or by placing a sample droplet onto the electrodes. The former approach is not practical in field measurements due to the difficulty of synchronizing the stirring and ASV procedures. The latter one shows limited sensitivity of measurement because pre-accumulation of analytes in stripping is limited by diffusion. Additionally, in this case, new electrodes are usually required for each measurement since it is difficult to remove the residue of deposited metals in a stagnant drop of solution before the next cycle of ASV.

It was demonstrated that μPEDs can be used in the selective measurement of Pb(II) in an aqueous mixture of Pb(II) and Zn(II) using SWASV. The designed of μPEDs was modified by introducing a pad of cellulose blotting paper as a sink in the outlet of the paper channel (FIG. 3c). The μPED allowed the continuous wicking of fluids to pass across the electrodes, and facilitated the plating of metals, as well as the cleaning of electrodes. By tuning the size of the cellulose blotting paper, the wicking time of fluids in the paper channel of μPEDs was optimized so that the flow stopped before the system entered the equilibration step in the process of SWASV.

Figure 8:
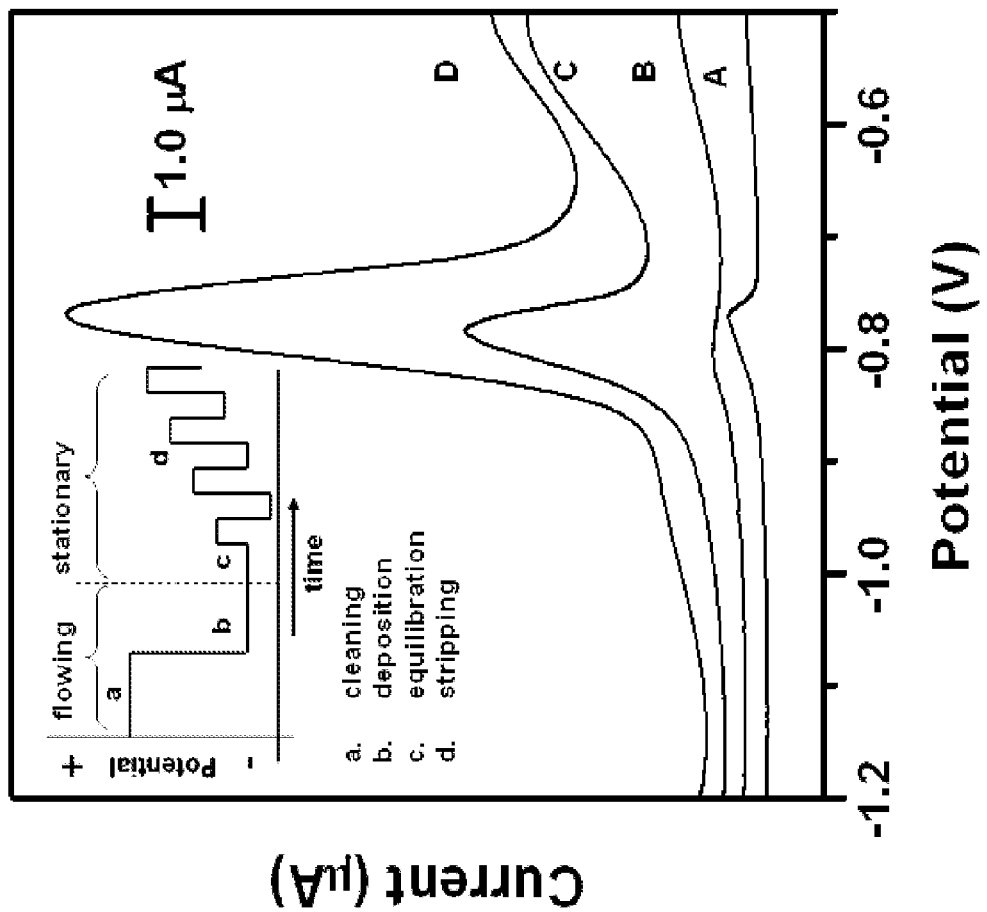
FIG. 8 illustrates Square-wave anodic stripping voltammograms for 25 ppb solution of Pb(II) in 0.1M acetate buffer (pH 4.5) in the presence of 25 ppb Zn(II): (A) a 100 µL solution placed directly on the electrodes; B) a 100 µL solution added to the stagnant µPEDs (without a pad of blotting paper as sink); (C, D) a solution of analytes continuously wicking the paper channel of the hydrodynamic µPEDs. The deposition time was 120 s (A, B, C) or 360 s (D)

FIG. 8 displays representative stripping voltammograms for the measurement of 25 ppb (μg/L) Pb(II) in acetate buffer solution in the presence of Zn(II). The voltammograms in the hydrodynamic μPEDs, in which the fluid of the sample solution continuously wicked in the paper microchannel, showed a well-defined, sharp peak for Pb(II) at ca. 780 mV versus the Ag/AgCl reference electrode (C and D in FIG. 8). In contrast, under the same SWASV conditions, a stagnant solution of analytes, both in the μPEDs (without a pad of blotting paper as a sink) and in an experiment that placed a droplet of sample solution on the electrodes, resulted in a much weaker signal (A in FIG. 8) or a poorly-defined response (B in FIG. 8). The hydrodynamic μPEDs thus exhibited a much higher sensitivity by a factor of five than the stagnant systems.

In the hydrodynamic μPEDs, the peak current of the analysis of Pb (II) dramatically increased with increasing the deposition time (FIG. 8). The peak current increased from 3.9 μA to 10.3 μA with the increase of deposition time from 120 s to 360 s. This increase was not obvious in the stagnant systems, since the deposition efficiency decays quickly with time due to the mass-transfer-limited reaction in the vicinity of the surface of electrodes. Moreover, it was found that the stagnant μPEDs showed a more poorly defined signal, compared to the system with a drop of sample solution directly placed onto the electrodes (FIG. 8). It is presumed that this is because the cellulose matrix in the stagnant μPEDs inhibits convective movement of the solutions, and thus affected the stripping behavior of Pb(II).

Figure 9:
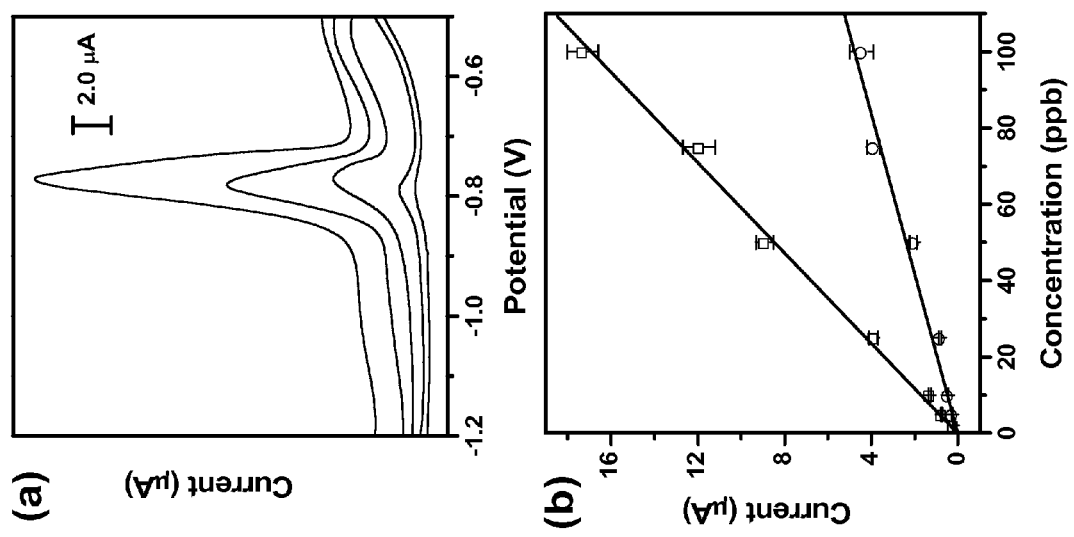
FIG. 9 illustrates: (a) square-wave anodic stripping voltammograms for the analysis of trace Pb(II) in 0.1M acetate buffer (pH 4.5) in the presence of Zn(II) (1:1 molar ratio of Pb(II) to Zn(II)) in the µPEDs with a solution of analytes continuously wicking along the paper channel. The concentrations (ppb) of Pb(II) (ascending along the y-axis) are 5, 10, 25, 50, and 100. The data are unsmoothed. (b) The resulting calibration plots for the analysis of trace Pb(II): a 100 µL solution of analytes placed on the electrodes (○), and a solution of analytes continuously wicking along the paper channel in the µPEDs (□)

The stripping voltammograms for the analysis of Pb(II) in the hydrodynamic μPEDs showed well-defined peaks and a strong signal over a wide range of concentrations of Pb(II); this level of performance offers convenient quantification of low ppb levels of lead (FIG. 9a). The peak intensity increased proportionally with the concentration of Pb(II), which yielded a highly linear calibration plot with a slope of 0.17 $\mu A \cdot ppb^{-1}$ for lead (correlation coefficient, 0.996) (FIG. 9b). The limit of detection of lead was estimated from the signal-to-noise characteristics of the data to be approximately 1.0 ppb (μg/L); this value is even lower than 2.5 ppb obtained in conventional systems with controlled stirring. This value is also much lower than the 10 ppb (μg/L) WHO guideline value for lead concentration in drinking water. It is believed that even lower concentrations of lead could be detected if longer deposition periods were used. The sensitive measurement of Pb(II) in the hydrodynamic μPEDs is highly reproducible, as indicated by the low relative standard deviation.

The performance of the hydrodynamic μPEDs for the analysis of lead was compared with the stagnant system, in which a drop of sample solution was placed on electrodes (FIG. 9b). The stagnant system exhibited a much lower sensitivity of 0.05 $\mu A \cdot ppb^{-1}$ for lead (correlation coefficient, 0.978), and a higher limit of detection of 4.3 ppb, than the dynamic measurement. Unlike the stagnant system, small perturbations (e.g., vibration, heating) did not interfere with the analysis of lead in the hydrodynamic μPEDs due to the stabilization of the flow of the sample solution by the paper matrix; this stabilization resulted in a high reliability and reproducibility of the measurements. The device can be reused by simply replacing the pad of blotting paper, since the continuous wicking removes dissolved analytes before the next cycle of the deposition of metals.

The Optimization of the Arrangement of Electrodes on the Paper Device

Figure 7:
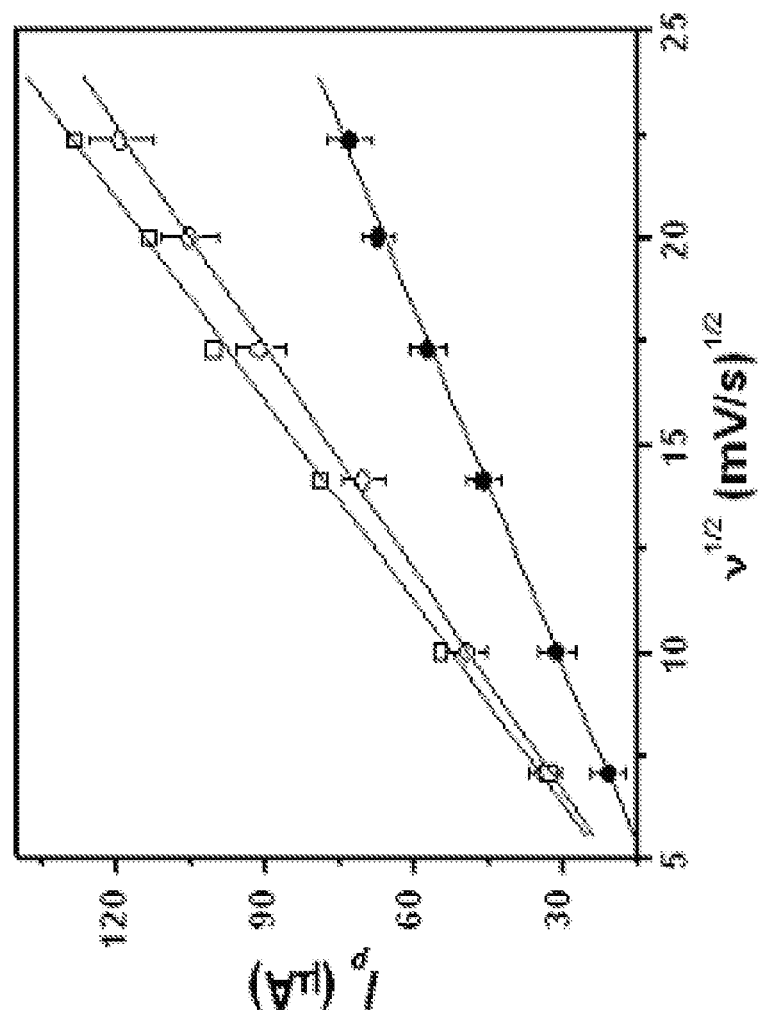
FIG. 7 illustrates a plot of anodic peak current against the square root of the scan rate, $v^{1/2}$, for CV experiments conducted on F-F µPEDs (empty square), S-S µPEDs (filled circles), and in bulk solutions (empty circles)

The performance of the μPED with different arrangements of the working and counter electrodes was compared. FIG. 7 shows a paper device with another geometry where the working and counter electrodes were placed face-to-face at top and bottom of the paper channel ("F-F μPED"). The device where working and counter electrodes were placed side-by-side beneath the paper channel is referred to as "S-S μPED."

FIG. 7 shows the peak current in CV experiments as a function of the square root of the scan rate, $v^{1/2}$. Under the same experimental conditions, the F-F μPED showed higher response currents in CV experiments, than did the corresponding S-S μPED. The F-F configuration probably has a higher effective surface area for electrochemical reactions can take place than the S-S configuration, since the electrochemical reactions take place between the two electrodes. The slope of the plot of the F-F μPED was close to that of the measurements in bulk solution. These results demonstrate that the configuration of electrodes influences the performance of the μPED, and that the paper material does not interfere with the electrochemistry. In terms of the spatial arrangement of electrodes, the flow passes through the working and counter electrodes in the F-F μPED at the same time, rather than in sequence as in S-S μPED. It is thought that the F-F μPED should show a performance superior in following the concentration of analytes flowing continuously in the paper channels. The F-F organization of electrodes also allows dense packing of sensors than S-S.

Performance of Gold Electrodes in the Paper-Based Devices

Figure 10:
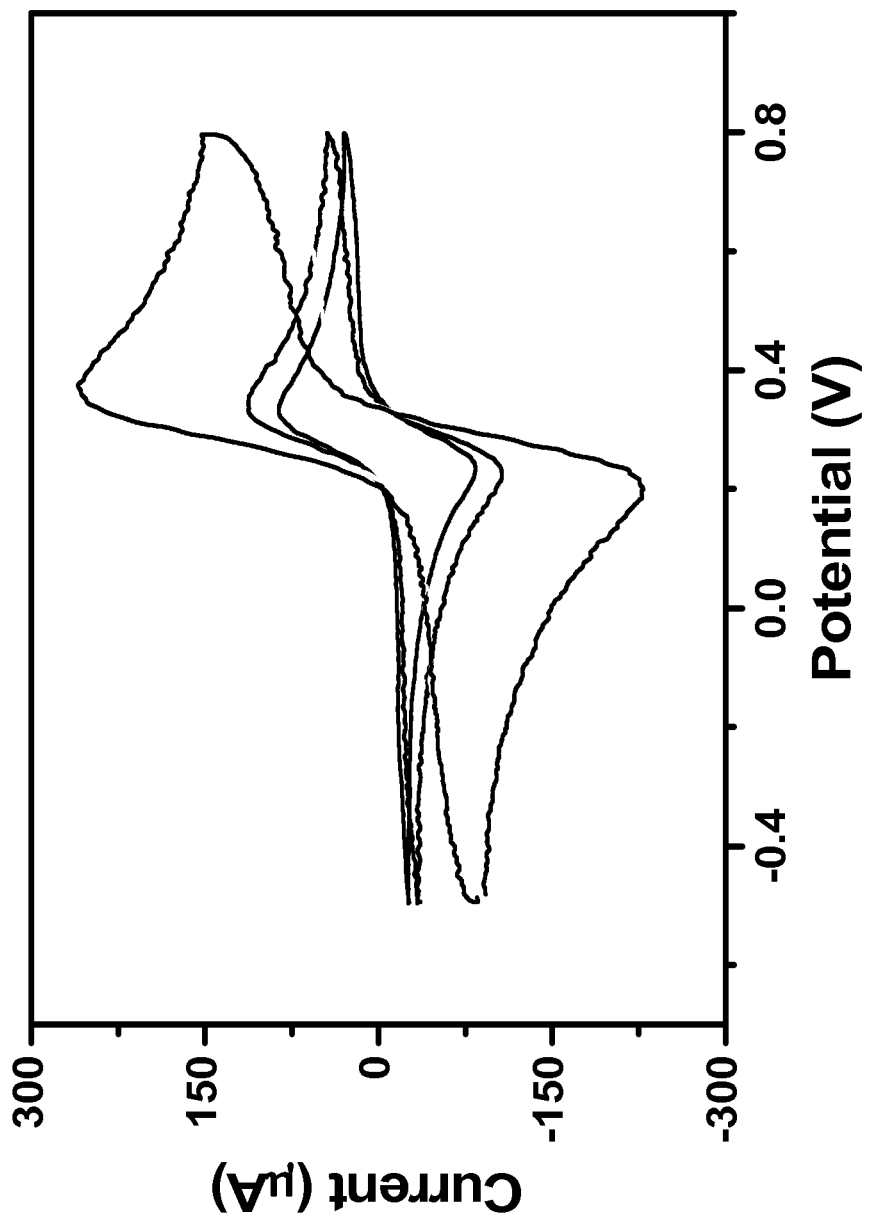
FIG. 10 illustrates reversible electrochemical reactions using Au as electrodes in the µPEDs.

Other types of electrodes, for example, gold stripes coated on plastics are also suitable for the paper-based electrochemical device, and may be used for specific applications. Paper devices with electrodes made from gold stripes showed excellent performance in cyclic voltammetry, but were less robust than the carbon-based electrodes. FIG. 10 shows that the electrochemical reactions were reversible on Au electrodes in the μPEDs.

The invention claimed is:

1. A microfluidic, electrochemical analysis device comprising:
   plural porous, hydrophilic layers, respectively separated by a fluid impermeable layer defining one or more openings in alignment with at least a portion of one or more hydrophilic channels within a hydrophilic layer to permit vertical fluidic communication through said fluid impermeable layer between said hydrophilic layers, wherein a porous, hydrophilic layer comprises a fluid sample deposition region and a patterned, fluid impermeable boundary that substantially permeates the thickness of the hydrophilic layer and defines the one or more hydrophilic channels therewithin in fluidic communication with said deposition region which permit fluidic flow within the one or more channels; and
   an electrode assembly comprising one or more electrodes in fluidic communication with said deposition region through the one or more hydrophilic channels, wherein said electrode assembly is disposed in fluidic communication with the one or more hydrophilic channels on one hydrophilic layer and a sample deposition region disposed on another hydrophilic layer.

2. The device of claim 1 wherein the electrode assembly is supported by or comprises a portion of said porous, hydrophilic layer.

3. The device of claim 1 wherein the device further comprises a substrate layer supporting the electrode assembly.

4. The device of claim 3 wherein the substrate comprises paper or plastic film.

5. The device of claim 1 wherein the fluid impermeable boundary further defines said sample deposition region.

6. The device of claim 1 further comprising a filter or an assay reagent in a hydrophilic channel.

7. The device of claim 1 wherein a said fluid impermeable layer comprises a polymer sheet or an adhesive sheet.

8. The device of claim 1 wherein said porous, hydrophilic layer comprises paper.

9. The device of claim 1 wherein said porous, hydrophilic layer comprises chromatography paper.

10. The device of claim 1 further comprising a fluid sink in fluidic communication with and downstream of one end of the hydrophilic channel and said electrode assembly enabling flow of a fluid through the hydrophilic channel and across said electrode assembly.

11. The device of claim 1 wherein the electrode assembly comprises an electrically conductive region of said hydrophilic layer surrounded at least in part by a fluid impermeable boundary.

12. The device of claim 1 wherein the fluid impermeable boundary comprises a wax or a polymerized photoresist.

13. The device of claim 1 wherein the electrode assembly comprises a working electrode and a counter electrode.

14. The device of claim 13 wherein the electrode assembly further comprises a reference electrode.

15. The device of claim 1 wherein the electrodes of said electrode assembly are arranged side by side on one of said hydrophilic layers.

16. A microfluidic, electrochemical analysis device comprising:
   plural porous, hydrophilic layers, respectively separated by a fluid impermeable layer defining one or more openings in alignment with at least a portion of one or more hydrophilic channels within a hydrophilic layer to permit vertical fluidic communication through said fluid impermeable layer between the hydrophilic layers, wherein a porous, hydrophilic layer comprises a fluid sample deposition region and a patterned, fluid impermeable boundary that substantially permeates the thickness of the hydrophilic layer and defines the one or more hydrophilic channels therewithin in fluidic communication with said deposition region which permit fluidic flow within the one or more hydrophilic channels; and
   an electrode assembly comprising one or more electrodes in fluidic communication with said deposition region through the one or more hydrophilic channels, wherein the electrode assembly comprises electrodes arranged facing one another in adjacent layers.

17. The device of claim 3 wherein an electrode of the electrode assembly is screen-printed on the substrate layer.

18. A method of determining the presence or concentration of one or more analytes in a fluid sample using a microfluidic, electrochemical device of claim 1, comprising:
   depositing a fluid sample onto said deposition region;
   permitting the sample to wick along a hydrophilic channel to provide fluidic contact of the sample with said electrode assembly; and
   measuring an electrochemical parameter with said electrode assembly as an indicator of the presence or concentration of an analyte in the sample.

19. The method of claim 18 wherein the electrochemical parameter is correlated with a concentration of an analyte.

20. The method of claim 18 wherein the electrochemical parameter is correlated with the presence of the one or more analytes.

21. The method of claim 18 wherein said sample deposition region is positioned over said electrode assembly.

22. The method of claim 18 wherein the microfluidic, electrochemical device further comprises
   a fluid sink in fluidic communication with a distal end of a said hydrophilic channel comprising a hydrophilic region in fluidic communication with the electrode assembly; and the method further comprising:
depositing a fluidic sample onto said deposition region disposed at a proximal end of a said hydrophilic channel; and
permitting transport of fluid in the sample through capillary action over the electrode assembly and into the fluid sink.

23. The method of claim 18 wherein measuring an electrochemical parameter comprises measuring impedance, current, or voltage.

24. The method of claim 18 wherein the step of measuring an electrical parameter is done by a method selected from the group consisting of amperometry, biamperometry, stripping voltammetry, differential pulse voltammetry, cyclic voltammetry, coulometry, chronoamperometry, and potentiometry.

25. The method of claim 18 wherein the analyte comprises glucose, cholesterol, uric acid, lactate, blood gases, DNA, haemoglobin, nitric oxide, or blood ketones.

26. The method of claim 18 wherein measuring an electrochemical parameter comprises anodic stripping voltammetry.

* * * * *